(12) United States Patent
Dong et al.

(10) Patent No.: US 8,175,703 B2
(45) Date of Patent: May 8, 2012

(54) CARDIAC RESYNCHRONIZATION THERAPY PARAMETER OPTIMIZATION

(75) Inventors: Yanting Dong, Shoreview, MN (US);
Yinghong Yu, Shoreview, MN (US);
Jiang Ding, Maplewood, MN (US);
Scott A. Meyer, Rochester, MN (US);
Xuan Wei, Roseville, MN (US);
Michael John Stucky, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1209 days.

(21) Appl. No.: 11/338,935

(22) Filed: Jan. 25, 2006

(65) Prior Publication Data
US 2010/0023078 A1    Jan. 28, 2010

(51) Int. Cl.
*A61N 1/362* (2006.01)
(52) U.S. Cl. .......................................... 607/9
(58) Field of Classification Search ........................ 607/9
See application file for complete search history.

(56) References Cited

U.S. PATENT DOCUMENTS

| | | | |
|---|---|---|---|
| 6,597,951 B2 * | 7/2003 | Kadhiresan et al. ............ | 607/9 |
| 6,832,113 B2 | 12/2004 | Belalcazar | |
| 7,113,823 B2 * | 9/2006 | Yonce et al. ..................... | 607/9 |
| 7,389,141 B2 * | 6/2008 | Hall et al. ......................... | 607/9 |
| 7,617,002 B2 * | 11/2009 | Goetz ........................... | 607/116 |
| 2002/0120311 A1 | 8/2002 | Lindh et al. | |
| 2003/0130581 A1 | 7/2003 | Salo et al. | |
| 2003/0144702 A1 | 7/2003 | Yu et al. | |
| 2003/0204212 A1 | 10/2003 | Burnes et al. | |
| 2004/0015081 A1 | 1/2004 | Kramer et al. | |
| 2004/0019365 A1 | 1/2004 | Ding et al. | |
| 2004/0127804 A1 | 7/2004 | Hatlestad et al. | |
| 2004/0138571 A1 | 7/2004 | Salo et al. | |
| 2004/0147966 A1 | 7/2004 | Ding et al. | |
| 2004/0158293 A1 | 8/2004 | Yonce et al. | |
| 2004/0181260 A1 | 9/2004 | Anderson et al. | |
| 2004/0186524 A1 | 9/2004 | Chinchoy | |
| 2004/0193223 A1 | 9/2004 | Kramer et al. | |

(Continued)

FOREIGN PATENT DOCUMENTS

EP    1350539 A1    10/2003

(Continued)

OTHER PUBLICATIONS

D. O'Donnell, V. Nadurata, A. Hamer, P. Kertes and W. Mohammed, *Long-term Variations in Optimal Programming of Cardiac Resynchronization Therapy Devices*, PACE 2005, 28: S24-26, Jan. 2005.

(Continued)

*Primary Examiner* — Carl H Layno
*Assistant Examiner* — Jeremiah Kimball
(74) *Attorney, Agent, or Firm* — Hollingsworth & Funk, LLC

(57) ABSTRACT

Systems and methods involve determination of CRT parameters using a number of CRT optimization processes. Each CRT optimization process attempts to return recommended parameters. The CRT parameters are determined based on the recommended parameters returned by one or more of the CRT optimization processes. The CRT optimization processes may be sequentially implemented and the CRT parameters may be determined based on the recommended parameters returned by a first CRT optimization process to return recommended parameters. The CRT parameters may be determined based on a combination of the recommended parameters returned. The CRT optimization processes implemented may be selected from available CRT optimization processes based on patient conditions.

26 Claims, 19 Drawing Sheets

U.S. PATENT DOCUMENTS

| | | |
|---|---|---|
| 2004/0220636 A1 | 11/2004 | Burnes |
| 2004/0220639 A1 | 11/2004 | Mulligan et al. |
| 2005/0038477 A1 | 2/2005 | Kramer et al. |
| 2005/0043895 A1 | 2/2005 | Schechter |
| 2005/0137629 A1 | 6/2005 | Dyjach et al. |
| 2005/0137632 A1 | 6/2005 | Ding et al. |
| 2005/0137634 A1 | 6/2005 | Hall et al. |
| 2005/0149136 A1 | 7/2005 | Siejko et al. |
| 2005/0149137 A1 | 7/2005 | Chinchoy et al. |
| 2005/0203579 A1 | 9/2005 | Sowelam et al. |
| 2005/0209649 A1 | 9/2005 | Ferek-petric |
| 2005/0209650 A1 | 9/2005 | Van Gelder et al. |
| 2005/0234517 A1 | 10/2005 | Braunschweig et al. |

FOREIGN PATENT DOCUMENTS

| | | |
|---|---|---|
| WO | 2005/011475 A2 | 2/2005 |
| WO | 2005/011802 A2 | 2/2005 |
| WO | 2005/056108 A2 | 6/2005 |

OTHER PUBLICATIONS

Office Action dated Dec. 18, 2009 from European Application No. 06839302.4, 3 pages.

Office Action Response dated Jun. 17, 2010 from European Application No. 06839302.4, 8 pages.

International Preliminary Report on Patentability dated Aug. 7, 2008 from PCT Application No. PCT/US2006/047216, 8 pages.

International Search Report and Written Opinion dated Apr. 24, 2007 from PCT Application No. PCT/US2006/047216, 15 pages.

* cited by examiner

CARDIAC RESYNCHRONIZATION THERAPY PARAMETER OPTIMIZATION

FIELD OF THE INVENTION

The present invention relates generally to cardiac resynchronization therapy (CRT), and more specifically, to methods and systems for optimization of CRT parameters.

BACKGROUND OF THE INVENTION

Congestive heart failure is the loss of pumping power of the heart, resulting in the inability to deliver enough blood to meet the demands of peripheral tissues. Congestive heart failure (CHF) may cause weakness, loss of breath, and build up of fluids in the lungs and other body tissues.

CHF is usually a chronic, long term condition, but can occur suddenly. It may affect the left heart, right heart or both sides of the heart. Deterioration of the muscles of the heart result in an enlargement of the heart and reduced contractility. The reduced contractility decreases the cardiac output of blood and may result in an increased heart rate. Heart rhythm conduction path block may also occur in enlarged heart tissue, causing the signals that control the heart rhythm to travel more slowly through the enlarged heart tissue. For example, if CHF affects the left ventricle, signals that control the left ventricular contraction are delayed, and the left and right ventricles do not contract simultaneously. Non-simultaneous contractions of the left and right ventricles decrease the pumping efficiency of the heart.

CHF may be treated by medication and/or by cardiac pacing therapy. Pacing therapy to promote synchronization of heart chamber contractions for improved cardiac function is generally referred to as cardiac resynchronization therapy (CRT). Some cardiac pacemakers are capable of delivering CRT by pacing of multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may be used to resynchronize the left and right ventricles. Bi-atrial pacing or pacing of all four heart chambers may alternatively be used.

Optimization of CRT parameters involves determining the pacing parameters, such as intervals between pacing pulses delivered to various heart chambers that provide effective CRT delivery. For the reasons stated above, and for other reasons stated below which will become apparent to those skilled in the art upon reading the present specification, there is a need in the art for methods and systems that provide for optimization of parameters for CRT. The present invention fulfills these and other needs.

SUMMARY OF THE INVENTION

The present invention is directed to systems and methods for determining cardiac resynchronization therapy (CRT) parameters. One embodiment involves a method for selecting CRT parameters that includes implementing a plurality of CRT optimization processes. Each CRT optimization process attempts to return recommended parameters for CRT. The CRT parameters are determined based on the recommended parameters returned by one or more CRT optimization processes of the plurality of CRT optimization processes.

According to one approach, the plurality of CRT optimization processes may be sequentially implemented and the CRT parameters may be determined based on the recommended parameters returned by a first CRT optimization process to return the recommended parameters. The plurality of CRT optimization processes may be sequentially implemented according to a predetermined order, or according to an order indicated by a physician, or according to a device-selected order.

According to another approach, a first one or more of the plurality of CRT optimization processes are implemented to define a search range for a second one or more of the plurality of CRT optimization processes.

Determining the CRT parameters may involve combining the recommended parameters returned by the one or more CRT optimization processes. In certain embodiments, a first one or more CRT optimization processes are implemented and a second one or more CRT optimization process are implemented if recommended parameters returned by the first one or more CRT optimization processes produce an ambiguity in CRT parameter selection.

The plurality of CRT optimization processes may be selectively implemented based on patient conditions or based at least in part on physician input. Determining the CRT parameters using parameter combinations or selective implementation of CRT optimization processes may also be based at least in part on physician input.

CRT may be delivered to a patient using the CRT parameters. The CRT parameters may include one or more of an atrioventricular delay, an interventricular delay, and an interatrial delay, for example.

Another embodiment is directed to a medical system. The system includes an input unit configured to receive recommended parameters for CRT returned by a plurality of CRT optimization processes. The system also includes a processor configured to determine CRT parameters based on the recommended parameters returned by one or more CRT optimization processes of the plurality of CRT optimization processes.

The system may further include a plurality of CRT optimization process modules. Each CRT optimization process module is capable of implementing a CRT optimization process that returns recommended parameters to the input unit.

The medical system may further include a control module. In one approach, the control module may automatically determine an order of implementation of the plurality of CRT optimization processes. According to another approach, the order of implementation may be determined based at least in part on input acquired through the user interface.

According to one aspect, the processor is configured to combine the recommended parameters returned by the one or more CRT optimization processes. The CRT parameters are determined based on the combined parameters.

According to other aspects, the processor is configured to select certain ones of the CRT optimization processes for implementation and/or is configured to select certain ones of the recommended parameters returned by the CRT optimization processes as the CRT parameters. According to a further aspect, some of the plurality of CRT optimization processes are selected for implementation based on patient conditions. According to further aspects, selection of CRT optimization processes for implementation and/or selection of recommended parameters as the CRT parameters may be based on physician input.

The medical system may include a CRT delivery module configured to deliver CRT using the CRT parameters. The CRT parameters may include one or more pacing parameters.

The medical system may include at least one component disposed within a housing of an implantable cardiac rhythm management system.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
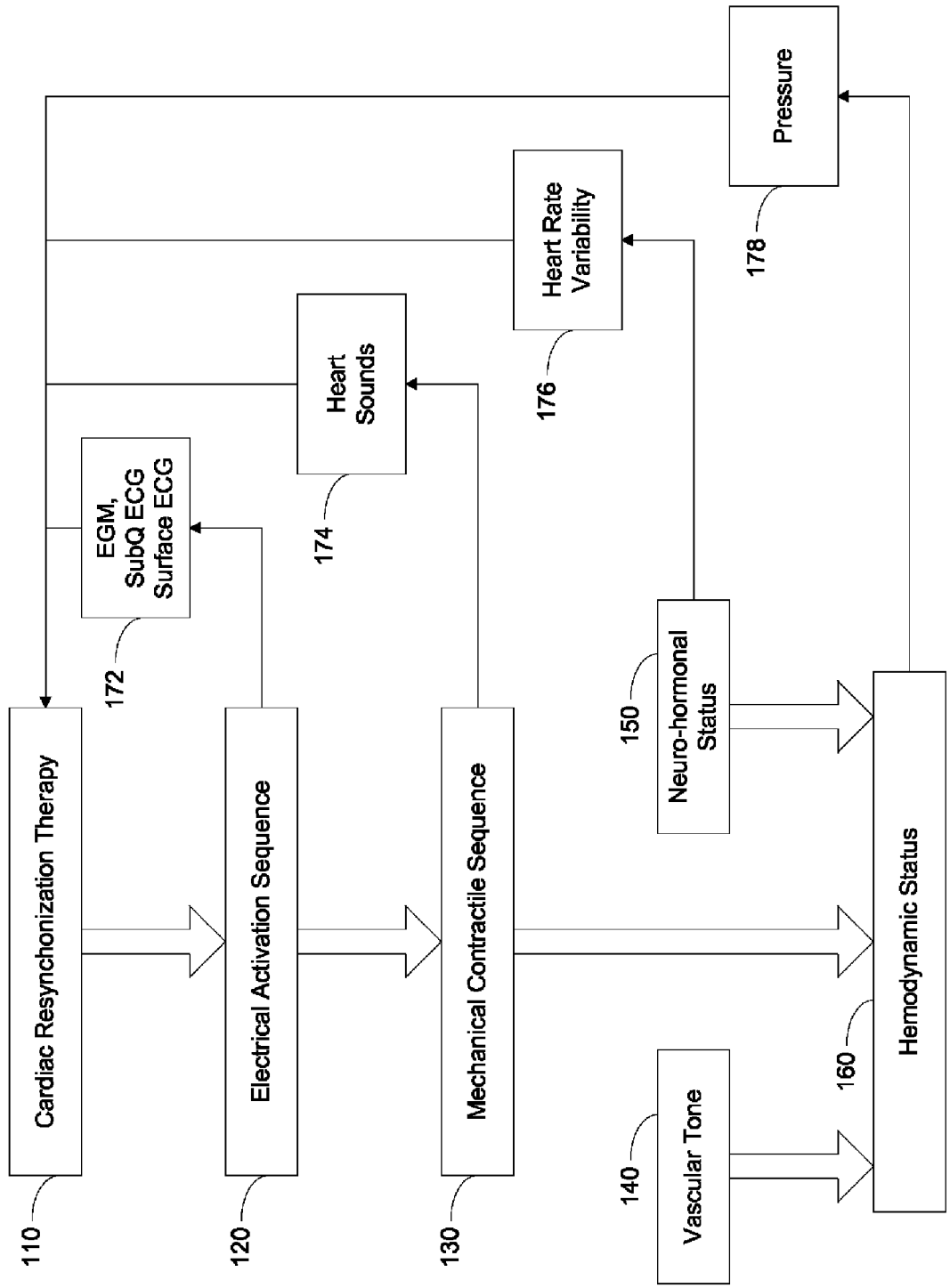
FIG. 1 is a flow diagram illustrating an exemplary set of physiological signals that may be used to determine parameters for CRT in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Methods, devices, and systems of the present invention provide for optimization of therapy parameters for cardiac resynchronization therapy (CRT). FIG. 1 is a flow diagram illustrating an exemplary set of physiological signals that may be used to determine parameters for CRT in accordance with embodiments of the invention. CRT 110 operates to change the electrical activation sequence 120 of the heart. For example, CRT, through cardiac pacing, changes the electrical activation sequence 120 by delivery of pacing pulses to multiple heart chambers. Modification of various pacing parameters, such as pacing energies, pacing waveforms, pacing delays, pacing sites, pacing modes, pacing rate limits, and/or other pacing parameters may be used to modify the electrical activation sequence 120 to enhance cardiac pumping function. Modification of the electrical activation sequence 120 changes the mechanical contractile sequence 130 of the heart. If effective, the CRT 110 improves the patient's hemodynamic status 160. The patient's vascular tone 140 and neurohormonal status 150 may also affect patient hemodynamics 160.

FIG. 1 provides an illustrative set of physiological signals related to CHF that may be used to determine parameters for effective delivery of CRT. Various CRT parameter optimization processes may analyze physiological signals and return recommended parameters for CRT optimization based on the analysis of the physiological signals. Recommended parameters for CRT returned by CRT optimization processes may include one or more cardiac pacing parameters such as atrioventricular delay, interventricular delay, interatrial delay, intersite pacing delays, pacing mode, tracking or non-tracking operation, pacing sites, pacing rate limits, or other pacing parameters, and/or non-pacing parameters, such as titrating the drugs being taken by the patients. The use of CRT optimization processes in accordance with embodiments of the invention may also provide information used to select sensing or impedance vectors which are best for the implementation of particular CRT optimization processes. This can be accomplished through interaction among different CRT optimization processes. In addition, the CRT optimization methodologies described herein may be used to reduce the number of CRT recipients who do not have a favorable response, through selecting the most appropriate cardiac pacing parameters.

The physiological signals used for CRT optimization may include cardiac electrical signals 172 including cardiac signals sensed internal to the heart, denoted electrograms (EGMs) and/or cardiac signals sensed external to the heart, denoted electrocardiograms (ECGs). From EGMs and/or ECGs 172, the heart's electrical activation sequence 120 can be determined. The EGM and/or ECG may show excessive delays and/or blockages in portions of the heart's electrical conduction system. Exemplary CRT optimization processes based on analysis of cardiac electrical signals are described in commonly owned U.S. Publication No. 2005/0137629 and U.S. Pat. Nos. 7,181,285, 7,013,176, 7,310,554, 7,389,141, and 7,113,823 which are incorporated herein by reference.

Physiological signals used for CRT optimization may include signals associated with the heart's mechanical contractile sequence 130. In one example, heart sounds 174, or generally energies resulting from the heart's mechanical vibrations, indicate the mechanical contractile sequence 130. One particular type of heart sound, known as the third heart sound, or S3, has been found to be associated with heart failure. For example, an increase in S3 activity may indicate elevated filling pressures which may result in the state of decompensated heart failure. S3 amplitude is related to the filling pressure of the left ventricle during diastole. The pitch, or fundamental frequency, of S3 is related to ventricular stiffness and dimension. Chronic changes in S3 amplitude may be correlated to left ventricular chamber stiffness and degree of restrictive filling. An exemplary CRT optimization process based on analysis of heart sounds is described in commonly owned U.S. Pat. Nos. 7,972,275 and 7,115,096 which are incorporated herein by reference.

Physiological signals used for CRT optimization may include heart rate from which heart rate variability may be derived. Heart rate variability (HRV) is the beat-to-beat variability in heart rate. The main component of HRV is respiratory sinus arrhythmia (RSA). Under resting conditions, the healthy individuals exhibit periodic variation in beat to beat intervals with respiration. The heart rate accelerates during expiration and slows during inspiration. Reduction in HRV 176 is a symptom of CHF and is related to compromised neurohormonal status 150. An exemplary CRT optimization process based on analysis of HRV is described in commonly owned U.S. Pat. No. 7,343,199 which is incorporated herein by reference.

Physiological signals used for CRT optimization may include blood pressure signals 178 which are directly related to hemodynamic status 160. In various examples, blood pressure may be sensed invasively or non-invasively and used to determine CRT parameters. For example, arterial pressure may be measured invasively by placing a pressure catheter in an artery, such as the radial artery. Left ventricular pressure may be measured via a pressure sensor inserted into the left ventricle. Non-invasive measurement of arterial pressure may be performed using a tonometer, phonocardiogram, or other methods. Pressure measurements obtained using these processes, or other processes, may be used to determine CRT parameters. Exemplary CRT optimization processes based on analysis of pressure signals are described in commonly owned U.S. Pat. Nos. 7,158,830, 6,666,826, and 7,409,244 which are incorporated herein by reference.

Other exemplary CRT optimization processes that may be used in conjunction with the methods and systems of the present invention are described in U.S. Pat. No. 7,206,634 which describes therapy optimization based on the use of mechanical sensors, U.S. Pat. No. 7,041,061 which describes therapy optimization based on quantification of wall motion asynchrony using echocardiographic images, U.S. Pat. No. 7,228,174 which describes therapy optimization based on impedance measurements, and U.S. Pat. No. 6,832,113, which describes therapy optimization based on a plethysmogram signal, all of which are incorporated herein by reference.

The present invention is directed to methods and systems for using multiple CRT optimization processes, such as those described in the above-referenced patent documents, and/or other CRT optimization processes, to determine CRT parameters. Each CRT optimization process is associated with particular strengths and weaknesses. For example, some CRT optimization processes may need to stop therapy during implementation, others may require an intact AV node, others may use a population based algorithm rather than an individualized procedure, still others may be sensitive to patient activity or posture, may have low resolution, and/or may be time-consuming in execution. The approaches of the present invention enhance CRT parameter determination through several techniques, including sequential implementation of a number of CRT optimization processes, combining the recommendations of a number of CRT optimization processes, and/or selecting CRT optimization processes or sensors to take into account patient conditions and/or to achieve targeted criteria. The methodologies of the present invention may be used to facilitate closed loop optimization of CRT parameters periodically, event-triggered or on demand.

Figure 2A:
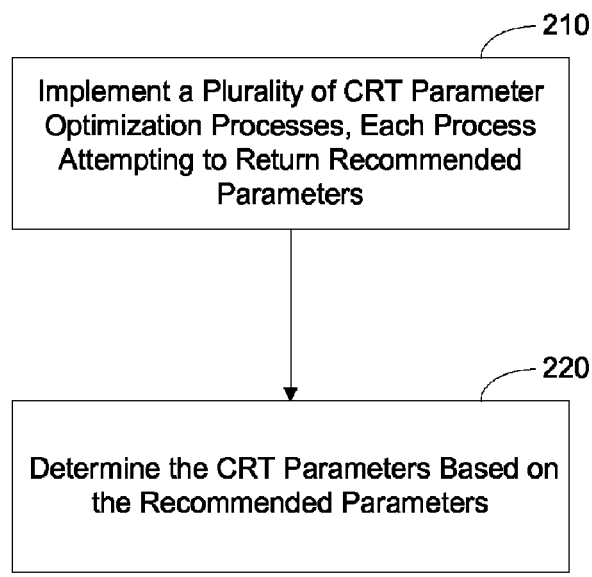
FIG. 2A is a flowchart of a method for determination of CRT parameters based on a combination of recommended parameters in accordance with embodiments of the invention.

According to one method, illustrated in the flowchart of FIG. 2A, a plurality of CRT optimization processes are performed 210, wherein each CRT optimization process attempts to return at least one recommended CRT parameter. The CRT parameters are determined 220 based on the recommended CRT parameters returned by one or more of the plurality of CRT optimization processes. For example, the CRT optimization processes may be sequentially performed. The CRT parameters may be determined based on the first CRT optimization process to return recommended parameters.

In another example, the recommended parameters of a first set of CRT optimization processes is used to narrow the search range of a second set of CRT optimization processes. The CRT parameters are determined based on the recommended CRT parameters of the second set of CRT optimization processes.

In yet another example, a first set of CRT optimization processes is used to recommend CRT parameters and a second set of CRT optimization processes is used to confirm the recommended CRT parameters of the first set of processes.

In a further example, the recommended parameters of one or more of the CRT optimization processes are combined to form the CRT parameters. The combination may be performed by mathematical processes, by selection of certain ones of the recommended parameters, or by a combination of techniques, for example.

Figure 2B:
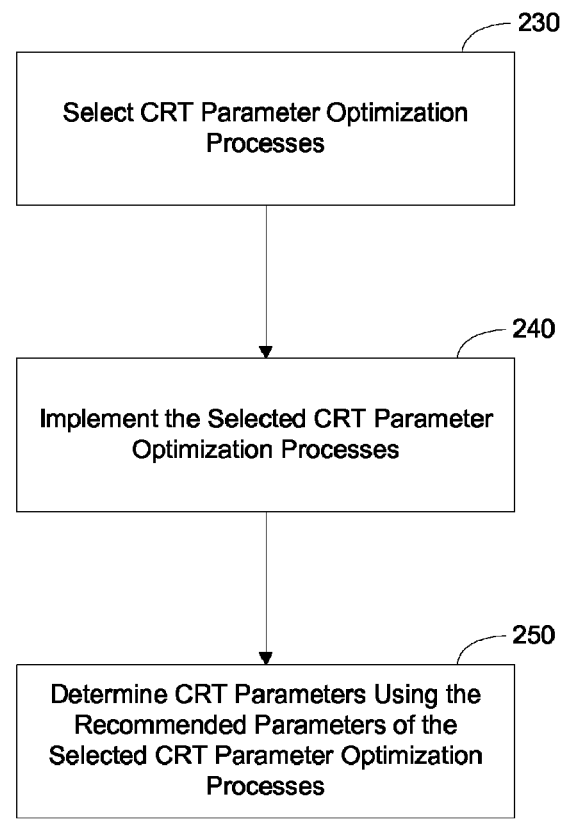
FIG. 2B is a flowchart of a method involving selective implementation of CRT optimization processes to determine CRT parameters in accordance with embodiments of the invention.

According to another method, illustrated in the flowchart of FIG. 2B, one or more CRT processes are selected 230 from a plurality of available CRT processes, each CRT process attempting to return recommended CRT parameters. The selected CRT processes are implemented 240. The CRT parameters are determined 250 based on the recommended parameters of the selected CRT processes.

CRT processes may be selected based on a variety of information acquired from one or multiple sources. For example, in some implementations, information may be acquired from one or more implantable or patient-external sensors configured to sense physiological variables. In other implementations, information may be acquired from an advanced patient management system that includes a database of information related to the patient and/or to CRT processes, such as medical history of the patient, clinical information associated with CRT or CRT processes, past history of success of various CRT optimization processes and/or sensors, and/or other information. Information useful in the implementation of CRT optimization may be input to the advanced patient management system via a user interface by the patient or by medical personnel, for example. Information from any combination of sources may be used to select CRT processes, may be used in connection with CRT parameter optimization, may be used to select sensors for CRT optimization processes, may be used to select parameters for CRT therapy and/or may be used to facilitate CRT therapy delivery, monitoring and/or control.

In one example, the CRT processes may be selected based on patient conditions, including activity level and/or cardiac electrical conduction status, such as AV block or left bundle branch block (LBBB). In another example, one or more CRT optimization processes are selected to recommend CRT parameters for one function (e.g., systolic function) and one or more other CRT optimization processes are selected to recommend CRT parameters for another function (e.g. diastolic function). The CRT parameters are determined based on the recommended CRT parameters from the selected processes.

Figure 2C:
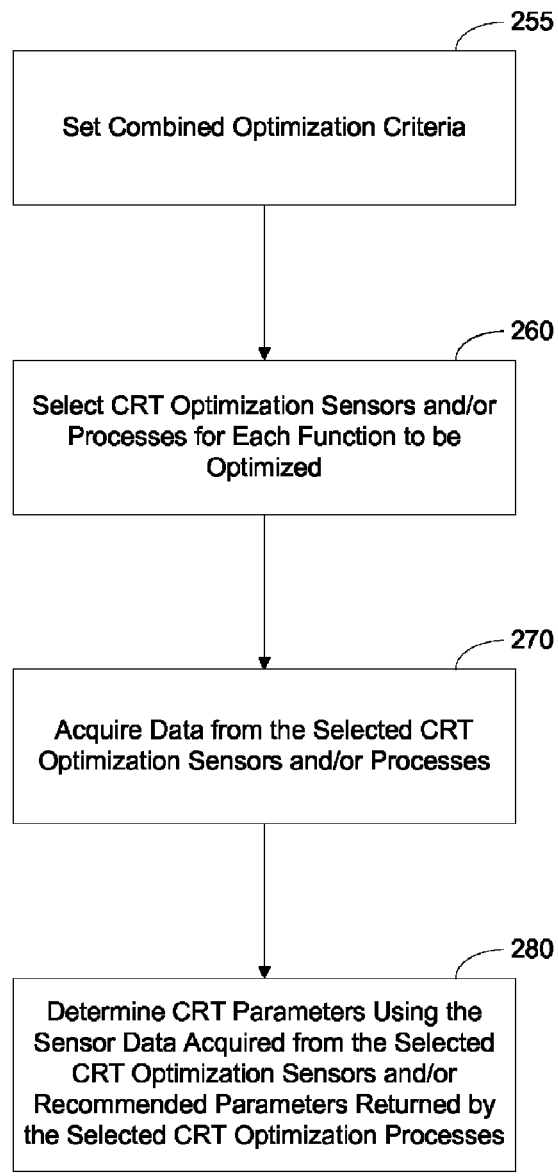
FIG. 2C is a flowchart of a method involving the use of a combined optimization criteria for determining CRT parameters in accordance with embodiments of the invention.

According to further embodiments, illustrated in the flowchart of FIG. 2C, CRT optimization sensors and/or CRT optimization processes used to determine the CRT parameters are selectable. Combined optimization criteria are determined 255. CRT optimization sensors and/or CRT optimization processes are selected 260 corresponding to each function targeted in the combined optimization criteria. Data is acquired 270 from the selected CRT optimization sensors and/or the selected CRT optimization processes return recommended parameters. The CRT parameters are determined 280 based on the data acquired from the CRT optimization sensors and/or the recommended parameters returned by the CRT optimization processes. For example, weighted optimization criteria for targeted functions related to CRT, such as systolic and diastolic function, may be specified by a physician or may be automatically specified by a cardiac medical device or system. Sensors and/or processes are selected for each targeted function. The CRT parameters are determined based on the acquired sensor data and/or the recommended parameters returned in accordance with the combined optimization criteria.

Figure 3:
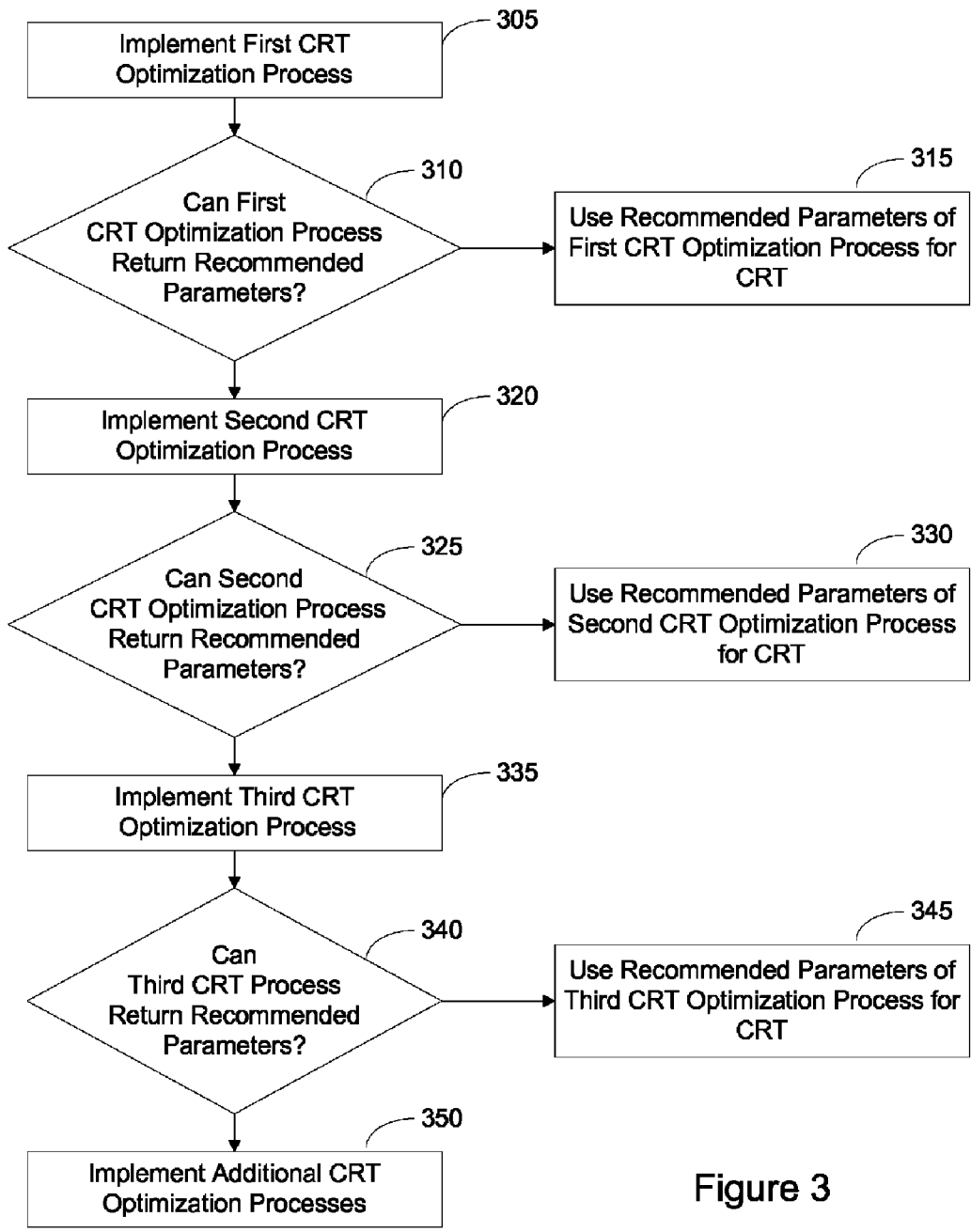
FIG. 3 is a flowchart illustrating sequential implementation of CRT optimization processes in accordance with embodiments of the present invention.

The flowchart of FIG. 3 illustrates determination of CRT parameters based on sequential implementation of a plurality of CRT parameter optimization processes in accordance with embodiments of the invention. A number of CRT optimization processes are implemented sequentially. When one CRT optimization process fails to recommend CRT parameters, a CRT optimization process next in the sequence is implemented. The optimization is complete when a CRT optimization process is able to return recommended CRT parameters. The optimization fails if none of the CRT optimization processes in the sequential list are able to return a recommendation. Failure of all of the optimization processes to return recommended parameters may indicate that the patient is a non-responder to CRT.

Turning now to FIG. 3, a first CRT parameter optimization process is implemented 305. If the first process is able to return 310 recommended CRT parameters, the recommended parameters of the first process are used 315 for CRT. If the first process is unable to return 310 recommended CRT parameters, a second process is implemented 320.

If the second process is able to return 325 recommended CRT parameters, the recommended parameters of the second process are used 330 for CRT. If the second process is unable to return 325 recommended CRT parameters, a third process is implemented 335.

If the third process is able to return 340 recommended CRT parameters, the recommended parameters of the third process are used 345 for CRT. If the third process is unable to return 340 recommended CRT parameters, additional CRT processes may be implemented 350 or CRT parameter optimization fails.

The order of implementation of the sequential CRT optimization processes may be implemented in a predetermined order. The order of implementation may be determined by a human analyst, or may be determined by a computer of an implantable or patient-external device. For example, the CRT optimization processes may be ranked based on targeted criteria with one or more best performing processes for the particular targeted criteria implemented first. Best performing processes may be based on one or more operating characteristics of the processes, such as speed, reliability, resolution, and/or other characteristics, with respect to the targeted criteria. For example, targeted criteria may involve one or more of AV synchrony, AA synchrony, VV synchrony, reverse remodeling, diastolic function, systolic function, and/or other criteria for CRT. The targeted criteria may be weighted if certain criteria are deemed to be more important than other criteria. Different targeted criteria or criteria weighting may produce a different order for implementation of the CRT optimization processes.

Figure 4:
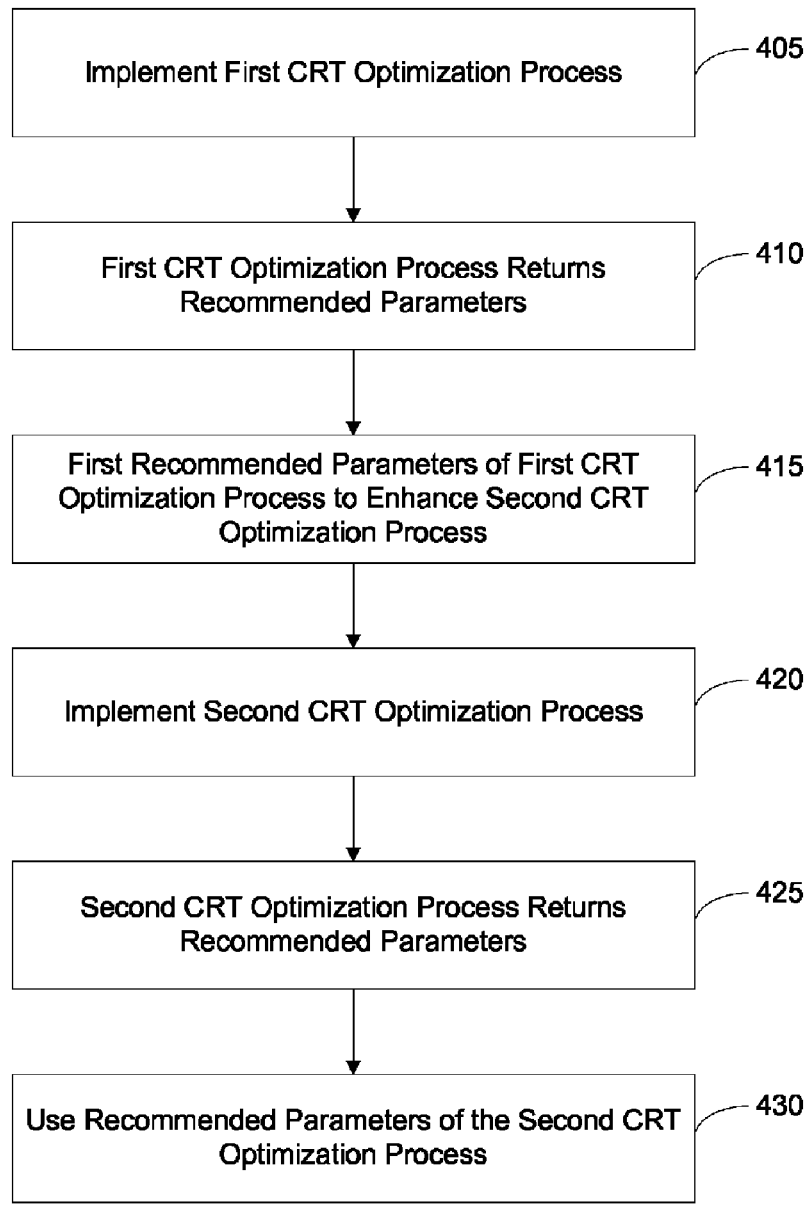
FIG. 4 is a flowchart illustrating the use of a first one or more CRT optimization processes to enhance a second one or more CRT optimization processes in accordance with embodiments of the invention.

FIG. 4 illustrates a method of implementing multiple CRT optimization processes for CRT parameter determination in accordance with another embodiment. In this embodiment, recommended parameters returned by one or more CRT optimization process are used to enhance operation of another one or more CRT optimization processes. The flowchart of FIG. 4 illustrates implementation of two CRT optimization processes, although any number of CRT optimization processes could be used. A first CRT optimization process is implemented 405 and returns 410 recommended parameters. The recommended parameters returned by the first process are used to enhance 415 a second CRT optimization process. The second CRT optimization process is implemented 420 and returns recommended CRT parameters 425. The recommended CRT parameters returned by the second CRT optimization process are used 430 for CRT.

In one example of this approach, recommended parameters returned by one CRT optimization process are used to set the parameter search range of a second process. In another example, recommended parameters returned by one CRT optimization process are used to confirm the recommended parameters returned by another CRT optimization process. In yet another example, recommended parameters returned by one CRT optimization process are used to resolve an ambiguity produced by another one or more CRT optimization processes.

Figure 5:
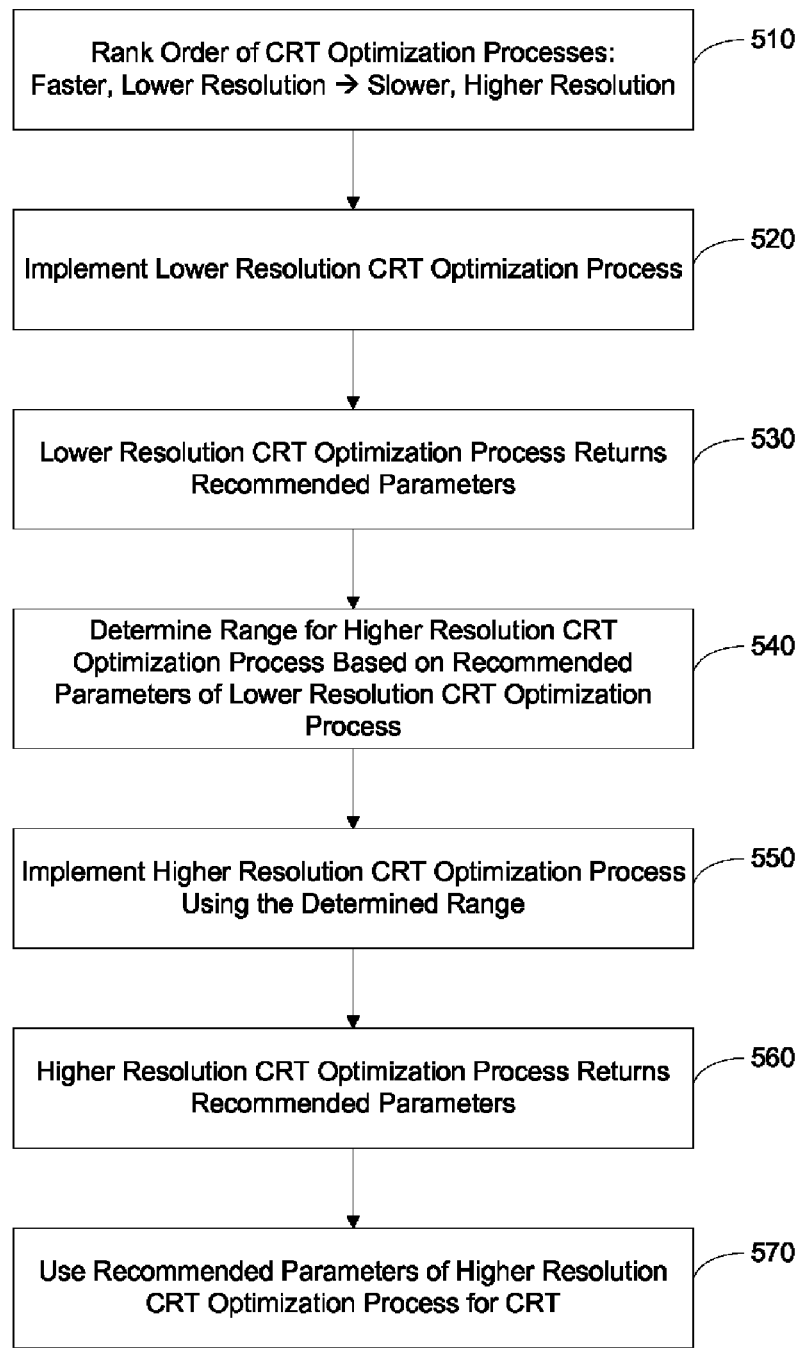
FIG. 5 is a flowchart illustrating the use of a first CRT optimization process to determine the range for a second CRT optimization process in accordance with embodiments of the present invention.

An example of using one or more CRT optimization processes to enhance other CRT optimization processes by narrowing the parameter search range is illustrated by the flowchart of FIG. 5. The available CRT optimization processes are ranked 510 according to resolution, with the lower resolution (faster) processes ranked for implementation before higher resolution (slower) processes. A lower resolution CRT optimization process is implemented 520 and returns 530 recommended parameters. The range of a higher resolution CRT optimization process is determined 540 based on the recommended parameters of the lower resolution process. The recommended parameters of the lower resolution process may be used to reduce and/or target the search range of the higher resolution process. The higher resolution process is implemented 550 using the range identified at block 540. The higher resolution process returns 560 recommended parameters which are used 570 for CRT. The method described in connection with FIG. 5 may be extended to the use of more than two CRT optimization processes with the range gradually refined as each CRT optimization processes is sequentially implemented.

In the example above, the CRT optimization processes are ranked according to resolution, although other characteristics may additionally or alternatively used for the ranking. For example, the CRT optimization processes may be ranked according to speed, reliability, history of success, amount of computing power required, and/or other characteristics.

In some embodiments, the recommended parameters returned by CRT optimization processes are combined to produce the parameters used for CRT. In various implementations, the CRT optimization processes may or may not be sequentially implemented and the recommended parameters returned by the CRT optimization processes may be combined to determine the CRT parameters.

CRT optimization processes may be classified into different categories. The categorization of CRT optimization processes may be based on different sensing signals (e.g., electrogram-based, hemodynamic sensor, neurohormonal sensor), based on different methods (morphology based, timing based), may be based on different targeted performance criteria (e.g., diastolic function (preload), systolic function (wall motion or dp/dt), neurohormonal response) may be based on different response time scale (e.g., acute pump function (LV dp/dt), chronic remodeling control (left ventricular end systolic volume (LVESV), left ventricular end diastolic volume (LVEDV))) or may be based on other categorization schemes. In one approach for selective implementation of CRT optimization processes, one or more CRT optimization processes from each category may be selected by a physician or may be device selected. The selected CRT optimization processes are implemented to make independent recommendations for CRT parameters. The recommended CRT parameters are combined to determine the CRT parameters to be used for therapy delivery. In another approach, selective implementation involves selection of a number of CRT optimization processes from the same category.

Figure 6:
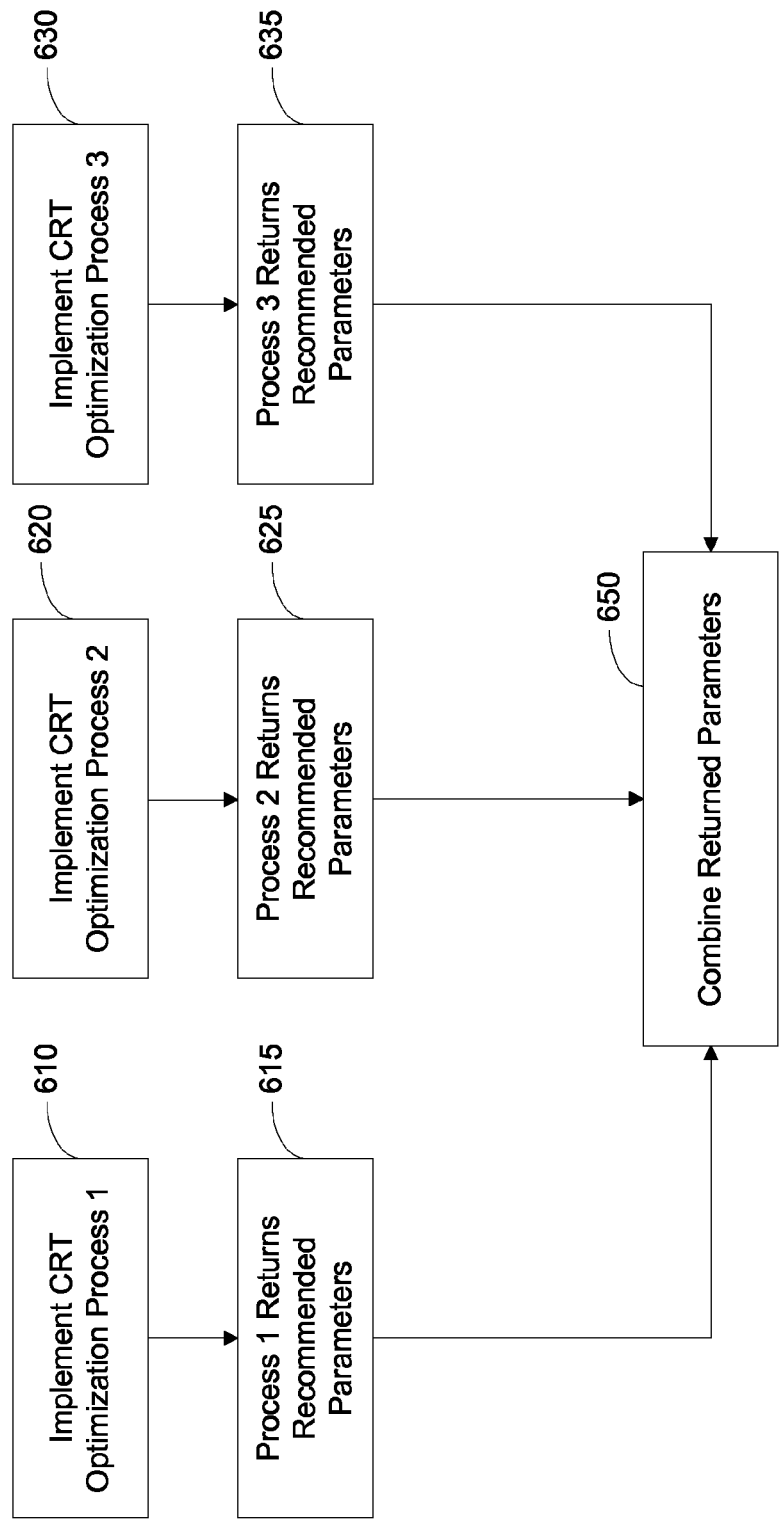
FIG. 6 is a flowchart illustrating a method for combining recommended parameters returned by CRT optimization processes in accordance with embodiments of the present invention.

An example of a combinatorial approach to CRT parameter determination is illustrated in the flowchart of FIG. 6 for three CRT optimization processes. First, second, and third CRT optimization processes are implemented 610, 620, 630. Each of the first, second, and third CRT optimization processes returns 615, 625, 635 recommended CRT parameters. The recommended parameters of the first, second, and third CRT optimization processes are combined 650 to produce the CRT parameters.

In one implementation of the method discussed in connection with FIG. 6, each of the first, second, and third CRT optimization processes optimize the same cardiac function, such as preload or contractility. Each process makes an independent recommendation for CRT parameters. The final CRT parameters are selected based on a combination of the recommendations made by the CRT optimization processes. For example, the recommendations may be combined by weighted average, voting, fuzzy logic, nonlinear mapping, by physician identified methods, or other methods.

In one implementation, the recommendations of the first, second, and third CRT optimization processes are presented to a human analyst who selects parameters for CRT from the recommended parameters.

In another implementation, the recommendations are combined based on a rules-based approach that may take into account clinical characteristics of the patient such as etiology and activity tolerance (e.g., based on NYHA classification), patient medication, and/or demographic characteristics such as age. The rules may be updated, for example, through an advanced patient management system, as the patient's status changes (medication levels, clinical characteristics) and/or as new information is acquired (updated demographic information).

In one example, recommended parameters returned by a first one or more CRT optimization processes are used to confirm other one or more CRT optimization processes. Confirmation is particularly useful when the CRT optimization processes used for confirmation optimize the same cardiac function as the primary CRT optimization process. Available CRT optimization processes may be organized in pairs or groups with a primary process in each pair or group. The primary CRT optimization process in a pair or group is implemented and returns recommended parameters. Another CRT optimization process in the same pair or group is implemented to confirm the results of the primary CRT optimization process.

Figure 7:
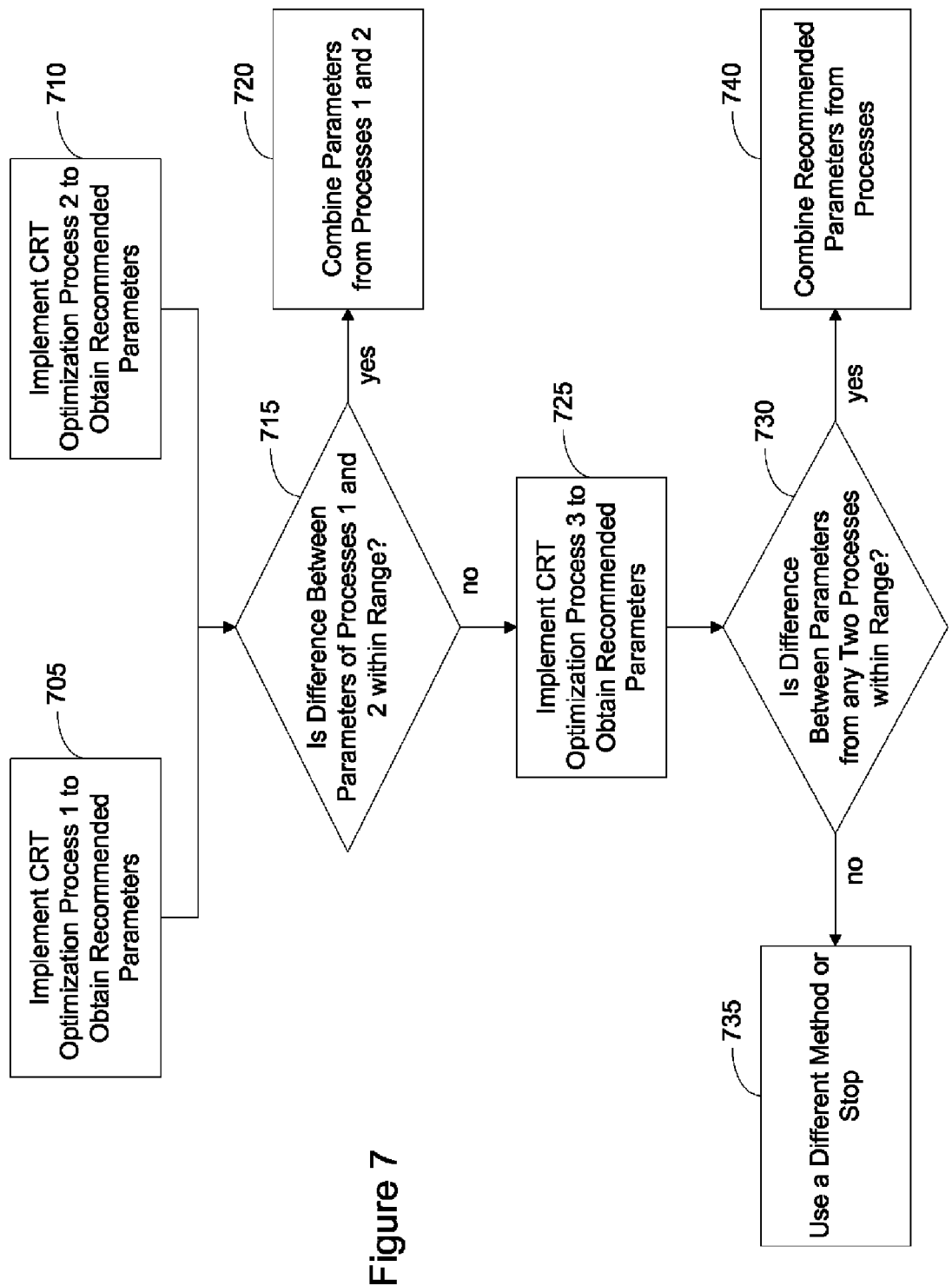
FIG. 7 is flowchart illustrating a method for using the results of some CRT optimization processes to confirm the results of other CRT optimization processes in accordance with embodiments of the invention.

In another example, illustrated in FIG. 7, confirmation is achieved if the difference between recommended parameters returned by at least two CRT optimization processes are within a predetermined range. First and second CRT optimization processes are implemented 705, 710 and each return recommended parameters. If the difference between the recommended parameters returned by the first and second CRT optimization processes are 715 within a predetermined range, the recommended parameters are combined 720 as previously described.

If the difference between the recommended parameters returned by the first and second CRT optimization processes are not 715 within the predetermined range, then a third CRT optimization process is implemented 725 and returns recommended parameters. If the difference between recommended parameters returned by any two of the three CRT optimization processes are within 730 the predetermined range, the recommended parameters of the two in-range CRT optimization processes are combined 740. If none of the three CRT optimization processes return parameters whose difference is within 730 the predetermined range, additional processes may be implemented, or CRT optimization fails 735. If the difference between recommended parameters of two or more CRT optimization parameters are beyond the predetermined range, a warning may be issued through an advanced patient management (APM) system or device programmer, for example.

In some embodiments, combination of CRT optimization processes is achieved by combination of recommended parameters for targeted cardiac functions. This approach involves the selection of CRT optimization processes, where each selected CRT optimization process optimizes a different a cardiac function. For example one CRT optimization process used in this approach may optimize systolic function, whereas another CRT optimization process may optimize diastolic function.

Each CRT optimization process makes an independent recommendation for CRT parameters. As previously discussed, the final CRT parameters may be determined based on a combination of the recommended parameters of the CRT optimization processes, such as a mathematical combination using weighted average, fuzzy logic, voting. In some implementations the combination method may be selected by the physician or the device. In some implementations, combination may be achieved by physician or device selection of certain ones of the recommended parameters.

Figure 8:
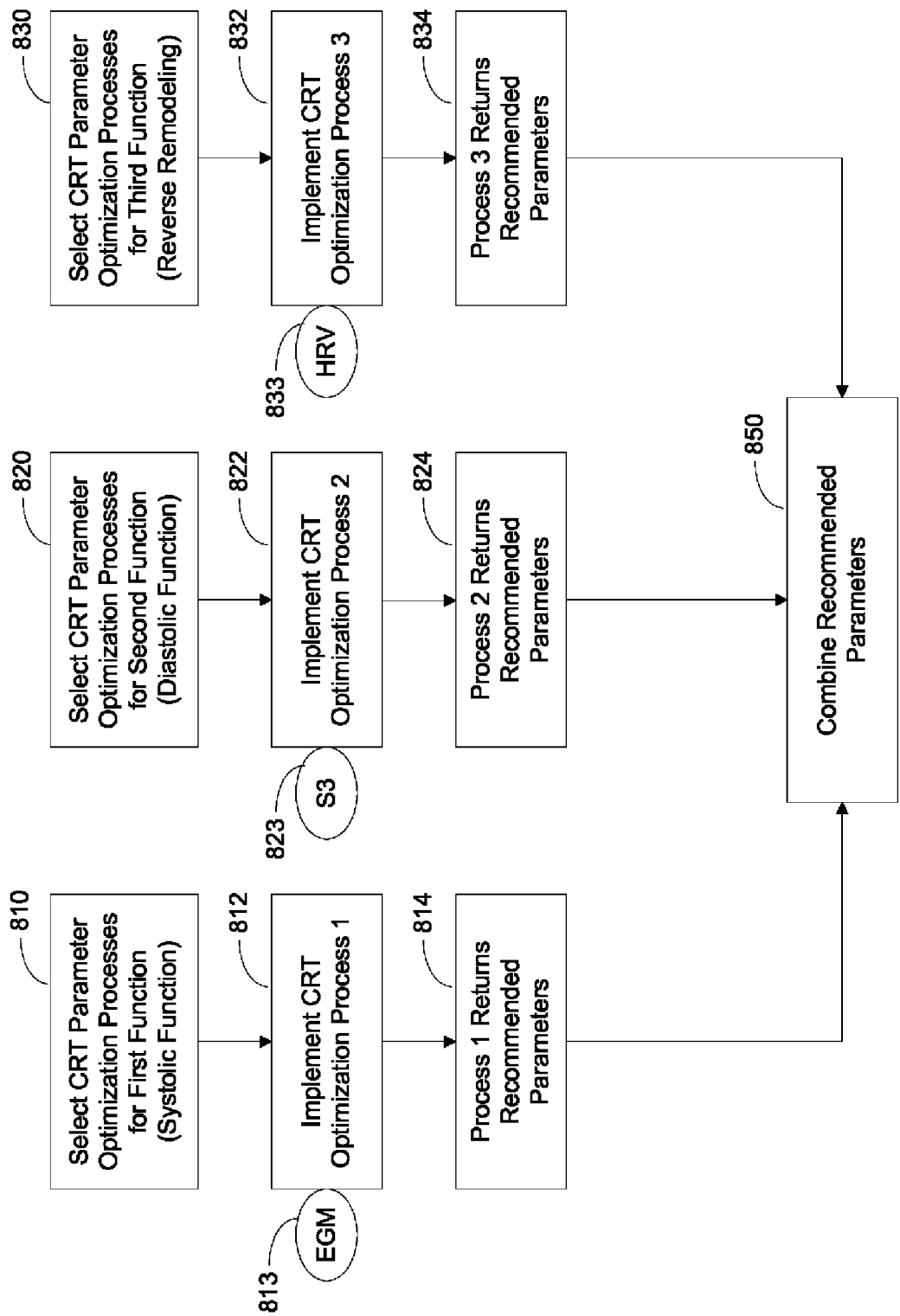
FIG. 8 is flowchart illustrating a method for determining CRT parameters based on CRT optimization processes selected for targeted functions in accordance with embodiments of the invention.

Combination of recommendations for targeted cardiac functions is illustrated in the flowchart of FIG. 8. In this example, the targeted functions for therapy optimization are systolic function, diastolic function, and reverse remodeling. A first CRT optimization process is selected 810 for systolic function. The CRT optimization process selected for systolic function may involve the use of an EGM sensor 813, for example. A second CRT optimization process is selected 820 for diastolic function. The CRT optimization process selected for diastolic function may involve the use of a heart sound sensor 823. A third CRT optimization process is selected 830 for reverse remodeling. The CRT optimization process for reverse remodeling may involve the use of an HRV sensor 833. The first, second, and third CRT optimization processes are implemented 812, 822, 832 and return 814, 824, 834 recommended parameters that optimize their targeted cardiac functions. The CRT parameters are determined 850 based on a combination of the recommended parameters of the first, second, and third CRT optimization processes.

Figure 9A:
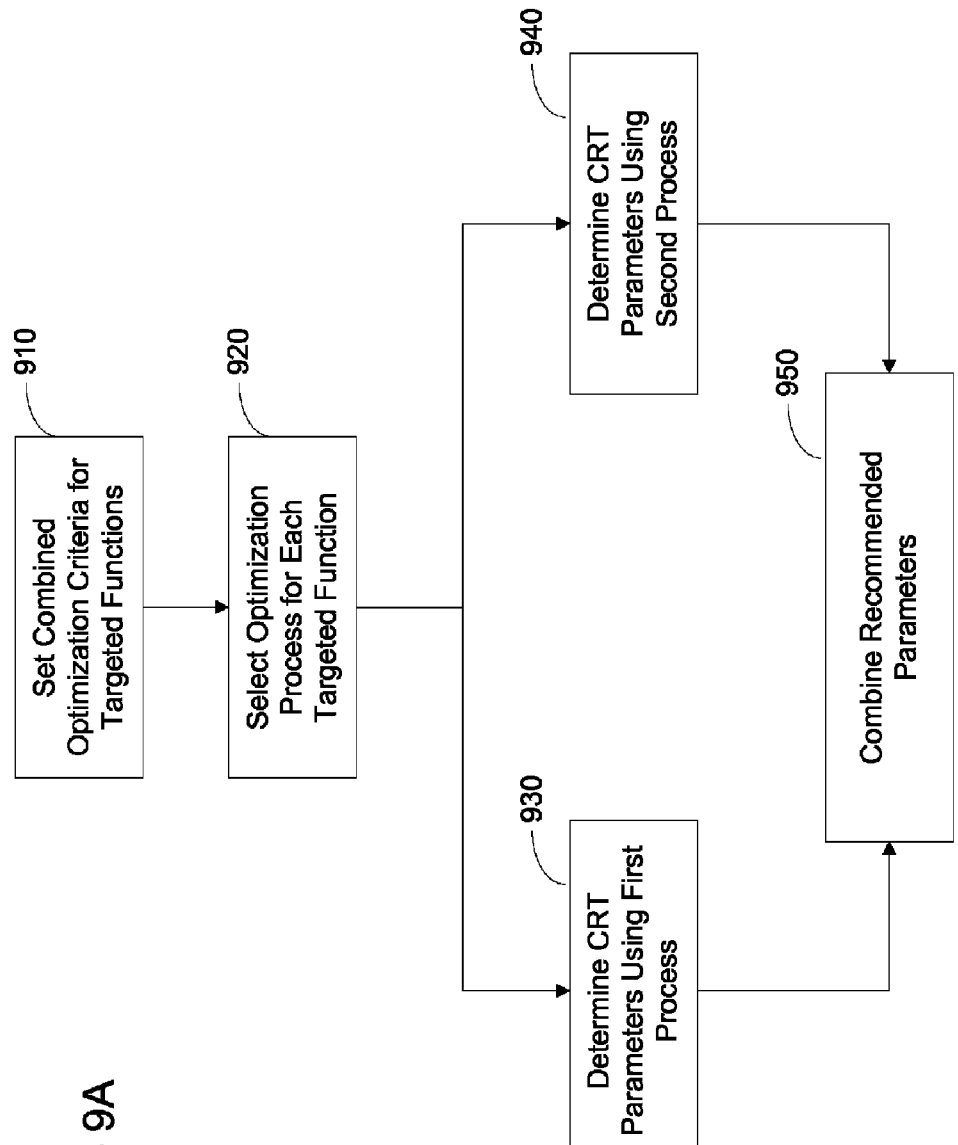
FIGS. 9A-9C are flowcharts of methods for determining CRT parameters to achieve combined optimization criteria for targeted functions in accordance with embodiments of the invention.
Figure 9B:
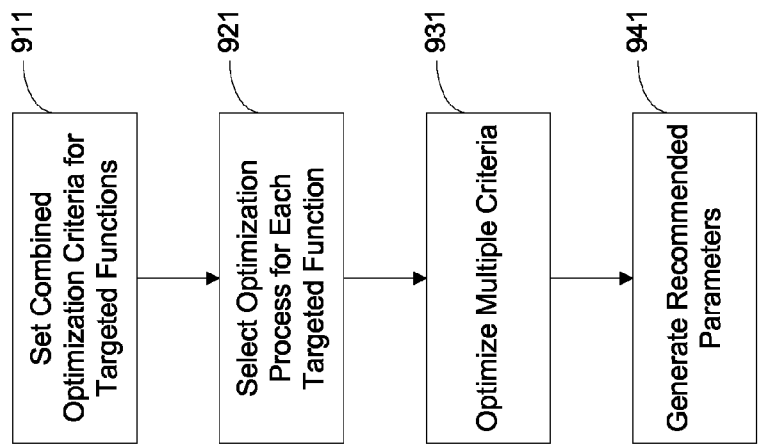
Figure 9C:
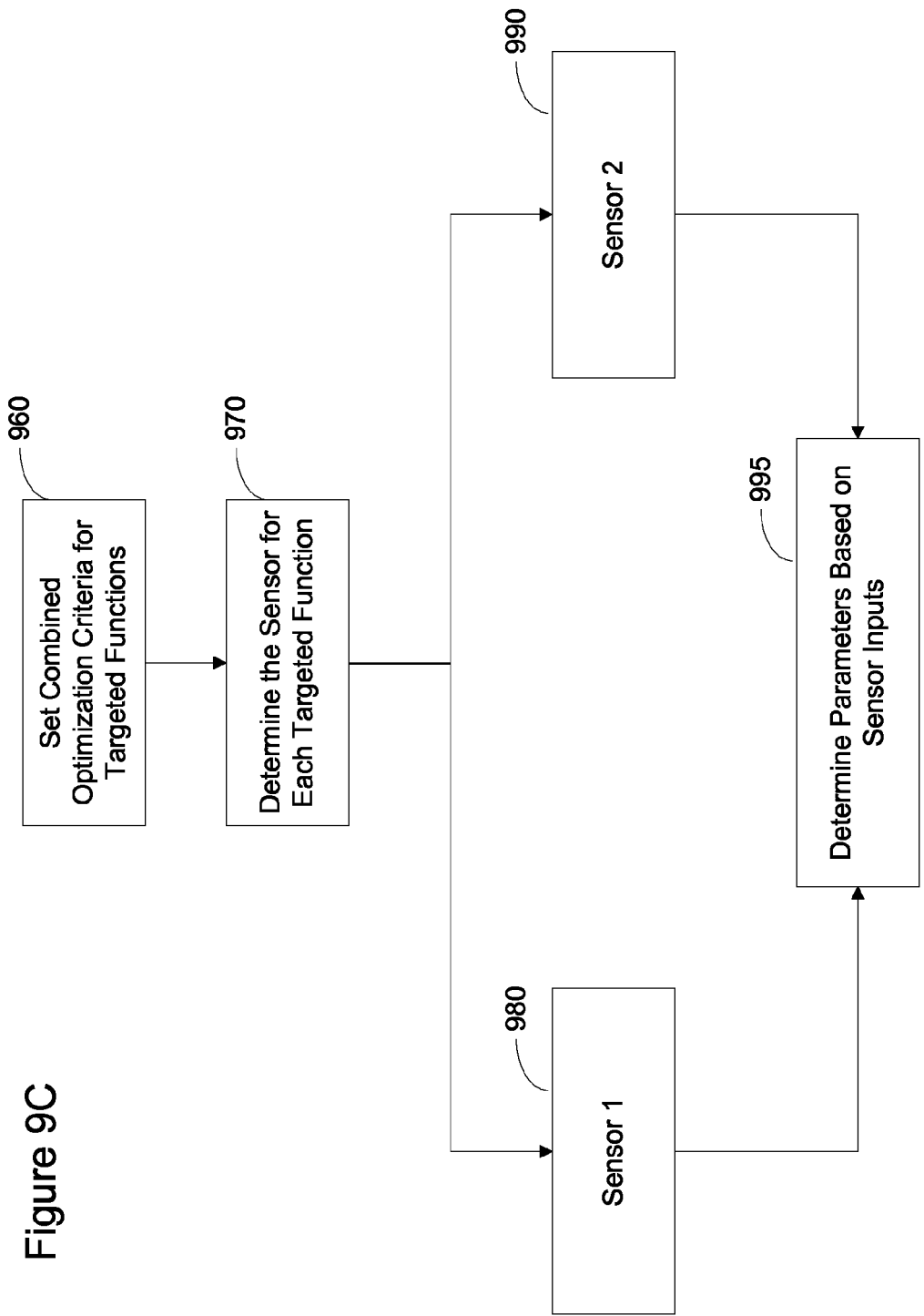

Some embodiments, such as the exemplary methods illustrated in the flowcharts of FIGS. 9A-9C involve the use of a combined optimization criteria that may be determined by a computer or human analyst. As illustrated in FIG. 9A, combined optimization criteria are set 910 for targeted functions. An example of targeted functions involves targeted diastolic and systolic functions with combined optimization criteria of 60% diastolic function and 40% systolic function. A CRT optimization process (or multiple processes) is selected 920 for each targeted function. The selected CRT optimization processes are implemented 930, 940 and return recommended parameters. The recommended parameters are combined 950, such as through the use of methods previously described.

Another approach involves optimization of multiple criteria in an integrated manner with respect to a combined optimization criteria. This approach is illustrated in FIG. 9B. Combined optimization criteria are determined 911 for targeted functions. A CRT optimization process (or multiple processes) is selected 921 for each targeted function. The optimization process is performed 931 in an integrated fashion, possibly simultaneously, to optimize the multiple criteria. The integrated optimization process generates 941 recommended CRT parameters.

Another approach involves the combination of sensor data to optimize CRT parameters. As illustrated in the flowchart of FIG. 9C, combined optimization criteria are set 960 for targeted functions. A sensor is selected 970 for each targeted function. For example, if the targeted functions are systolic and diastolic functions, an EGM sensor may be used for systolic function and a heart sound sensor is used for diastolic function. Relative changes in the sensor measurements provide surrogate for the systolic or diastolic function measurement. Other methods using the sensor measurements may also be used as the surrogates for the targeted function. Data is acquired using the selected sensors 980, 990. The CRT parameters are determined 995 based on a combination of the sensor data to optimize the targeted function.

In some embodiments, CRT optimization processes are selected for implementation based on patient conditions. For example, certain CRT optimization processes may only be used, or are more effective, for patients having an intact AV, other CRT optimization processes are suitable for patients having AV block. Still other CRT optimization processes are more effective than others for patients with atrial fibrillation (AF) or inter atrial block. The specific patient conditions may be detected by patient condition sensors, for example, sensors coupled to an implantable device, such as a pacemaker, or to a patient-external device, such as an advanced patient management system. Alternatively, or additionally, information useful for CRT optimization, including patient conditions and/or other factors such as past historical information, patient medical history, physiological information, non-physiological information, contextual information, questionnaire information and/or other information may be input through a user interface to the implantable and/or patient-external device. Information from any combination of sources may be used to facilitate the selection of CRT optimization processes to be implemented, the sensors used for implementation of the CRT optimization processes, the optimization or selection of CRT therapy parameters, the control of CRT therapy based on the parameters, and/or other processes for configuring or delivering CRT therapy, for example.

Figure 10A:
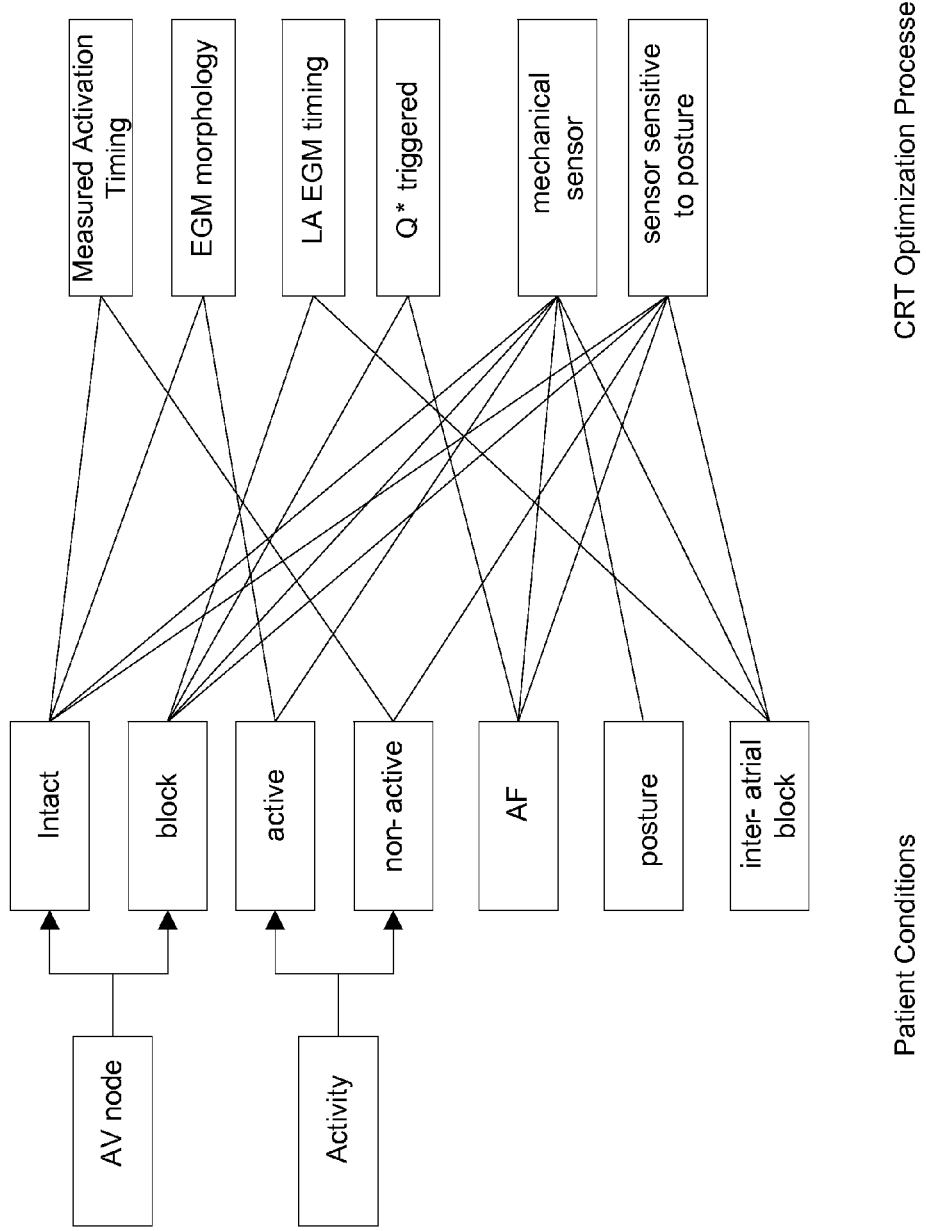
FIGS. 10A-10C are diagrams illustrating selection of CRT optimization processes based on patient conditions in accordance with embodiments of the invention.
Figure 10B:
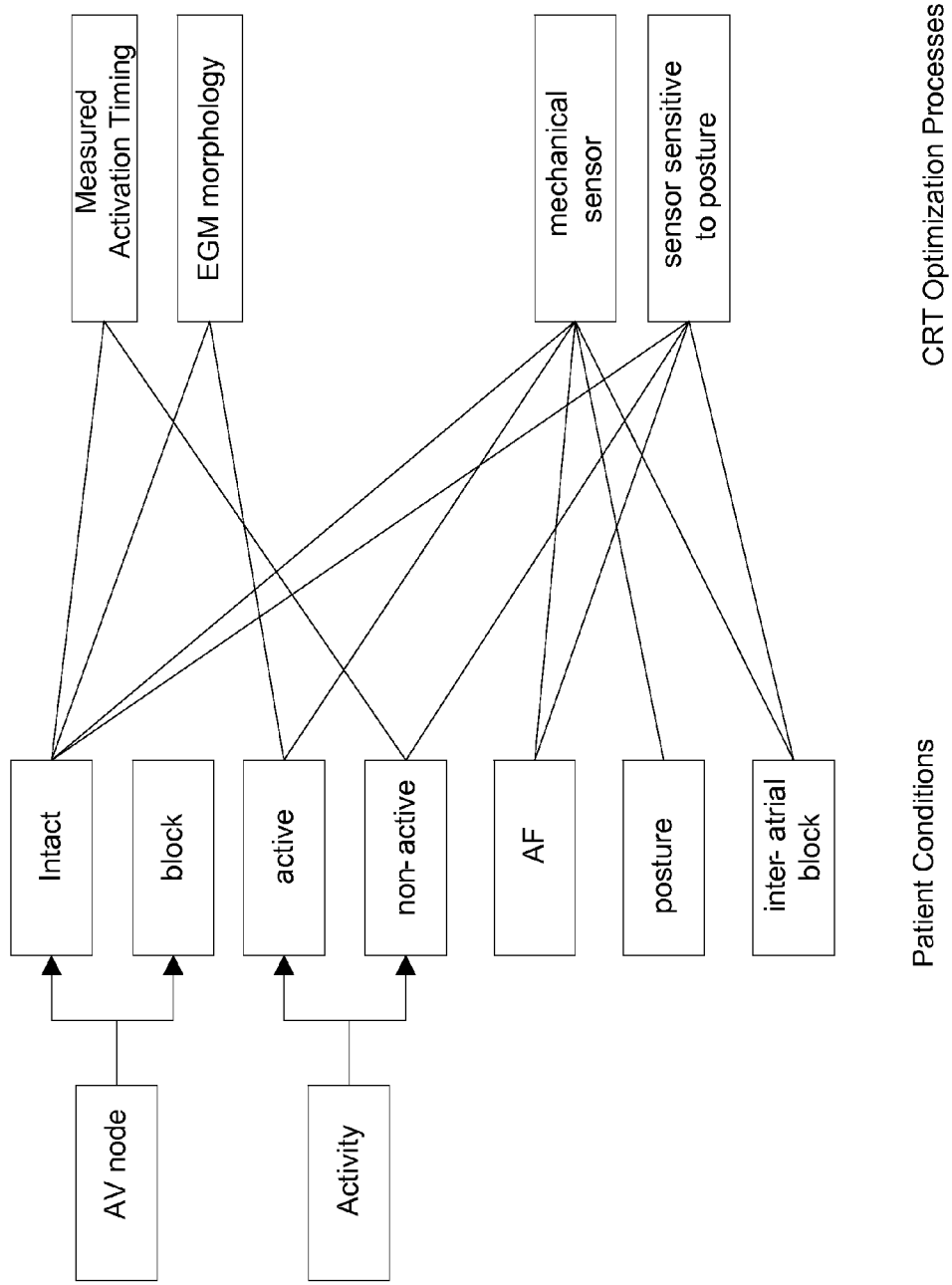
Figure 10C:
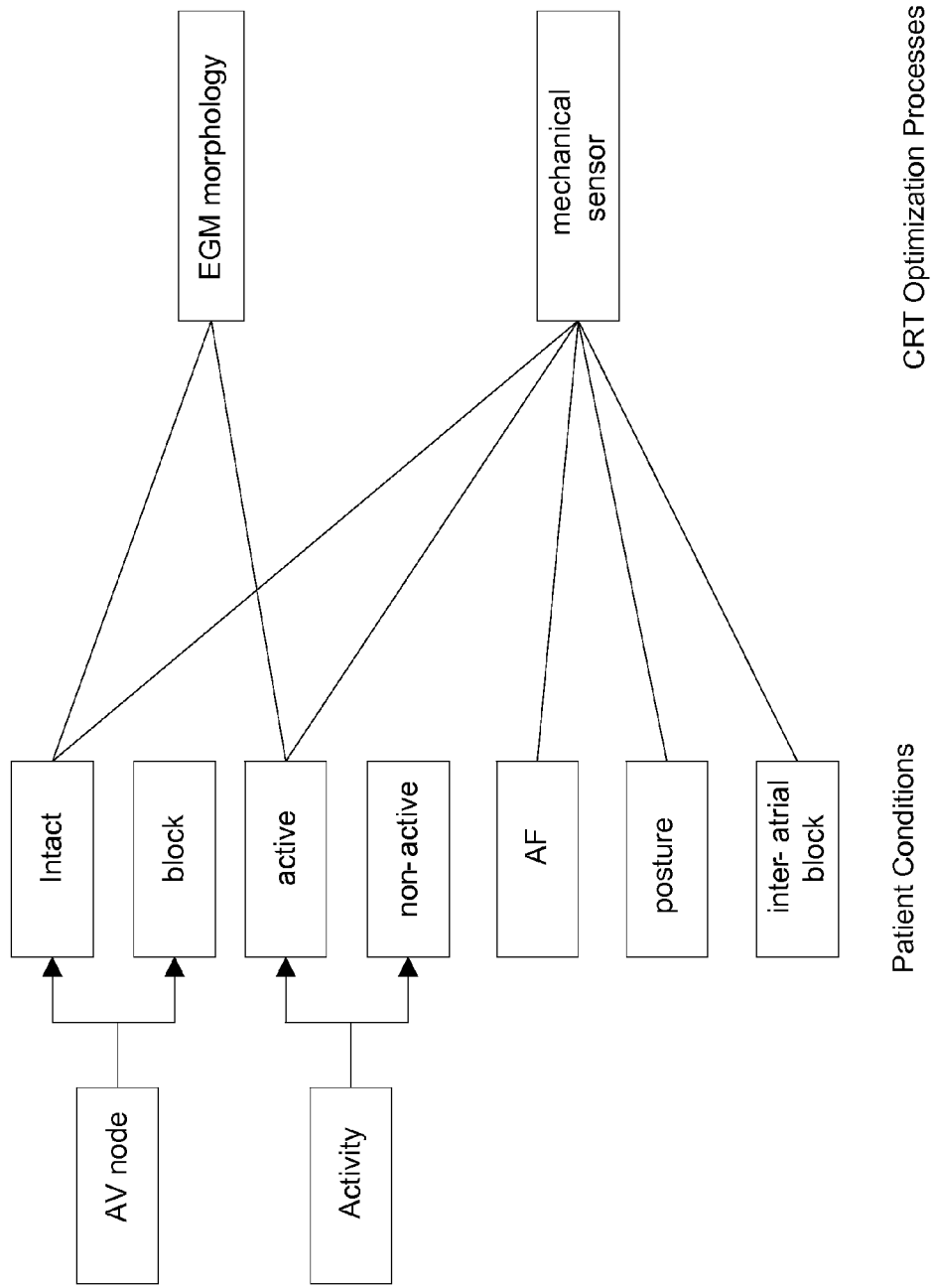

FIGS. 10A-10C illustrate automatic selection of CRT optimization processes based on patient conditions. On the left side of FIG. 10A, an exemplary set of patient conditions that may affect CRT optimization processes are listed. The exemplary set of patient conditions includes AV node status (intact or blocked), patient activity (active or inactive), atrial fibrillation (AF), posture, and inter-atrial block.

On the right side of FIG. 10A, various CRT optimization processes are listed. The exemplary set of CRT optimization processes include processes based on measurement of activation timing, processes based on EGM signal morphology, processes based on left atrial (LA) EGM timing, pre-excitation based processes (Q* triggered), processes based on mechanical sensor signals, and processes sensitive to posture changes (such as heart sound, impedance and/or pressure-based techniques). Lines connecting the patient conditions to the CRT optimization processes indicate processes that are more suitable for patients having the associated patient conditions. For example, CRT optimization processes based on measurement of activation timing and CRT optimization processes sensitive to posture changes are suitable for inactive patients; EGM morphology processes and CRT optimization processes based on mechanical sensors are compatible with active patients.

As an example, consider that a hypothetical patient has an intact AV node. The AV node status may be determined, for example, based on information entered into a device via a user interface, or may be automatically detected by an AV node sensor, or by other methods. Processes involving measurement of activation timing and EGM morphology are suitable for patients with intact AV node. LA EGM timing-based processes, pre-excitation based processes, are suitable for patients with AV block. Processes involving mechanical sensor measurements or posture sensitive measurements are suitable for situations of either intact AV or blocked AV node. FIG. 10B illustrates the patient condition/CRT optimization process table with the processes more suitable for patients with AV block removed and the processes more suitable for patients with intact AV node remaining.

Continuing the hypothetical example, consider that activity sensors determine that the patient is currently active. Two CRT optimization processes are suitable for active patients with intact AV node. FIG. 10C illustrates all CRT optimization processes removed except the remaining suitable CRT optimization processes. The CRT optimization processes suitable for the patient are EGM morphology processes and CRT optimization processes based on mechanical sensor measurements.

Figure 11:
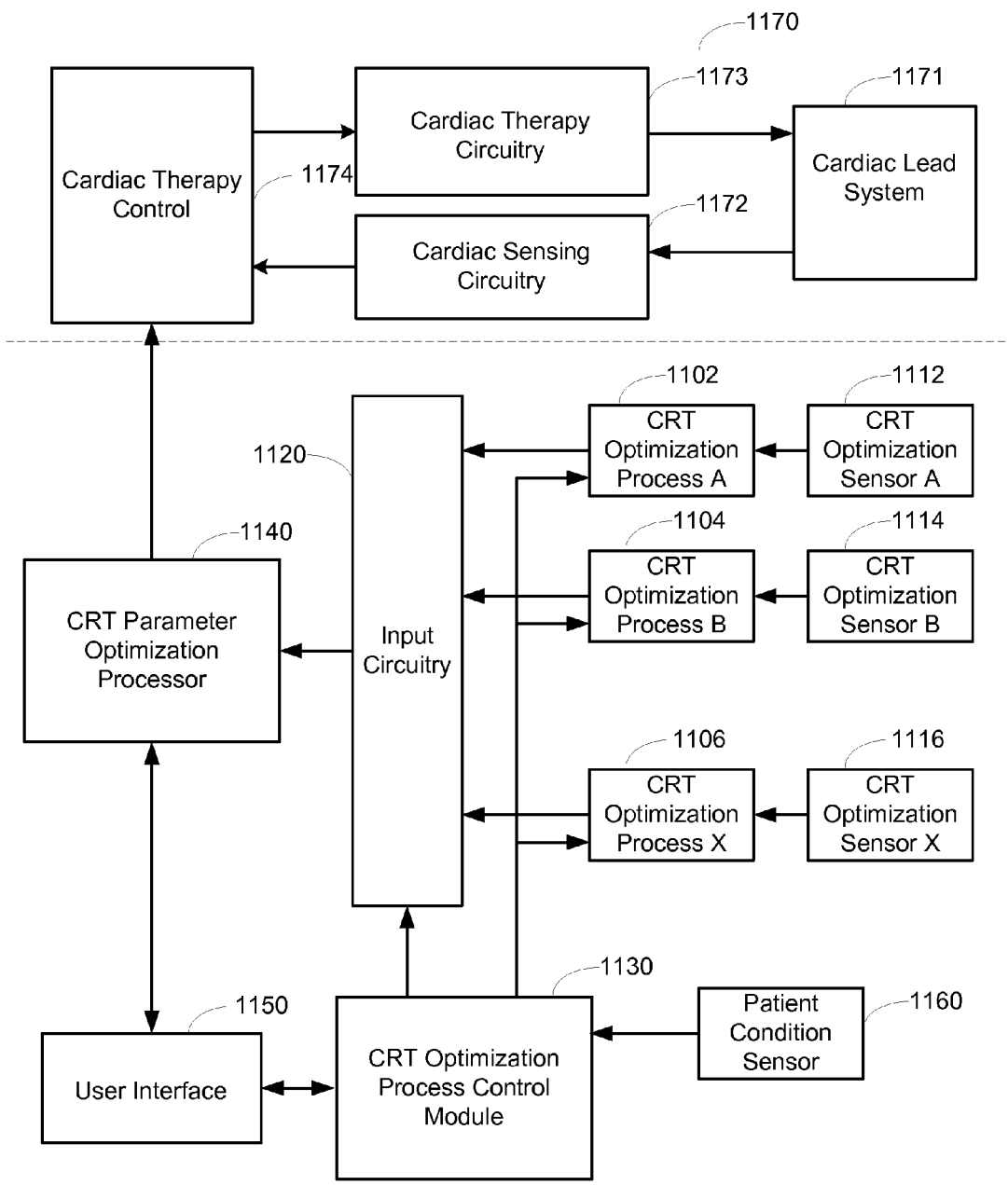
FIG. 11 is a block diagram a medical system for determining CRT parameters in accordance with embodiments of the present invention.

FIG. 11 is a block diagram of a system capable of implementing methods for CRT parameter determination according to embodiments of the present invention. An optional cardiac rhythm management (CRM) system 1170 is also illustrated.

FIG. 11 shows a number of CRT optimization process modules 1102, 1104, 1106 coupled to their respective CRT optimization sensors 1112, 1114, 1116. For example CRT optimization process A 1102 may involve CRT parameter optimization based on HRV and associated CRT optimization sensor A 1112 may comprise an HRV sensor. CRT optimization process B 1104 may involve CRT parameter optimization based on EGM morphology and associated CRT optimization sensor B 1114 may comprise an EGM sensor. It is to be understood that a particular CRT optimization process may use multiple sensors. Furthermore, the sensors 1112, 1114, 1116 may be used by the CRT optimization process modules 1102, 1104, 1106 in various configurations, e.g., multiple sensors can be used in conjunction with a particular CRT optimization process and/or a particular sensor can be used in conjunction with multiple CRT optimization processes.

In some embodiments, the CRT optimization processes performed by process modules 1102, 1104, 1106 return recommended parameters to the CRT parameter optimization processor 1140 via the input circuitry 1120. The CRT parameter optimization processor 1140 determines the CRT parameters based on a combination of the recommended parameters.

In some embodiments, the CRT optimization processes performed by optimization process modules 1102, 1104, 1106 may be selectably implemented by a CRT optimization process control module 1130. In these embodiments, the selected CRT optimization process modules 1102, 1104, 1106 return their recommended parameters to a CRT parameter optimization processor 1140 via input circuitry 1120. The CRT parameter optimization processor 1140 determines CRT parameters based on the recommended CRT parameters provided by the CRT optimization process modules 1102, 1104, 1106.

In other embodiments, the CRT optimization processes performed by process modules 1102, 1104, 1106 may be ranked by the CRT optimization process control module 1130. In these embodiments, the CRT optimization processes implemented by modules 1102, 1104, 1106 are implemented in ranked order, and return their recommended parameters to a CRT parameter optimization processor 1140 via input circuitry 1120. The CRT parameter optimization processor 1140 determines CRT parameters based on recommended CRT parameters provided by the ranked CRT optimization processes.

In further embodiments, the CRT optimization process modules 1102, 1104, 1106 are not used. The CRT optimization process control module 1130 may select one or more CRT optimization sensors 1112, 1114, 1116. Signals from the selected CRT optimization sensors 1112, 1114, 1116 are input via the input circuitry 1120 to the CRT parameter optimization processor 1140. The CRT parameter optimization processor 1140 determines CRT parameters based on a combination of the sensor signals.

In some configurations, the CRT optimization process control module 1130 perform selection or rankings of CRT optimization processes 1102, 1104, 1106 and/or CRT optimization sensors 1112, 1114, 1116 based on user input acquired through a user interface 1150. In other configurations, the CRT optimization process control module 1130 performs selection or rankings of CRT optimization processes 1102, 1104, 1106 and/or CRT optimization sensors 1112, 1114, 1116 based on patient conditions determined using patient condition sensors 1160, which may include an activity sensor, for example. In still other configurations, a combination of user input and patient conditions may be used to select or rank CRT optimization processes 1102, 1104, 1106 and/or CRT optimization sensors 1112, 1114, 1116.

In some embodiments, the CRT parameter optimization processor 1140 may be coupled to a therapy unit, such as the CRM system 1170 illustrated in FIG. 11. The CRM system may be capable of sensing and pacing one, some or all heart chambers, and/or multiple sites within a single heart chamber. The CRM system 1170 includes cardiac leads 1171 having electrodes coupled to the heart. Cardiac sensing circuitry 1172 is coupled to the cardiac leads 1171. The cardiac sensing circuitry 1172 and cardiac leads 1171 are used for sensing cardiac electrical activity. Cardiac therapy circuitry 1173 delivers electrical stimulation to the heart through the cardiac leads 1171. A cardiac therapy control processor 1174 controls the operation of the sensing and pacing circuitry 1172, 1173 and other functions of the CRM 1170. Output signals from the CRT parameter optimization processor 1140 may be used to control pacing parameters for CRT delivered by the CRM system 1170.

In some embodiments, components of the CRT parameter optimization system illustrated in FIG. 11 may be implemented in a patient implantable device. In other embodiments, components of the CRT parameter optimization system may be implemented in a patient external device. In still other embodiments, some of the components of the CRT parameter optimization system may be implantable while others are patient-external.

Figure 12:
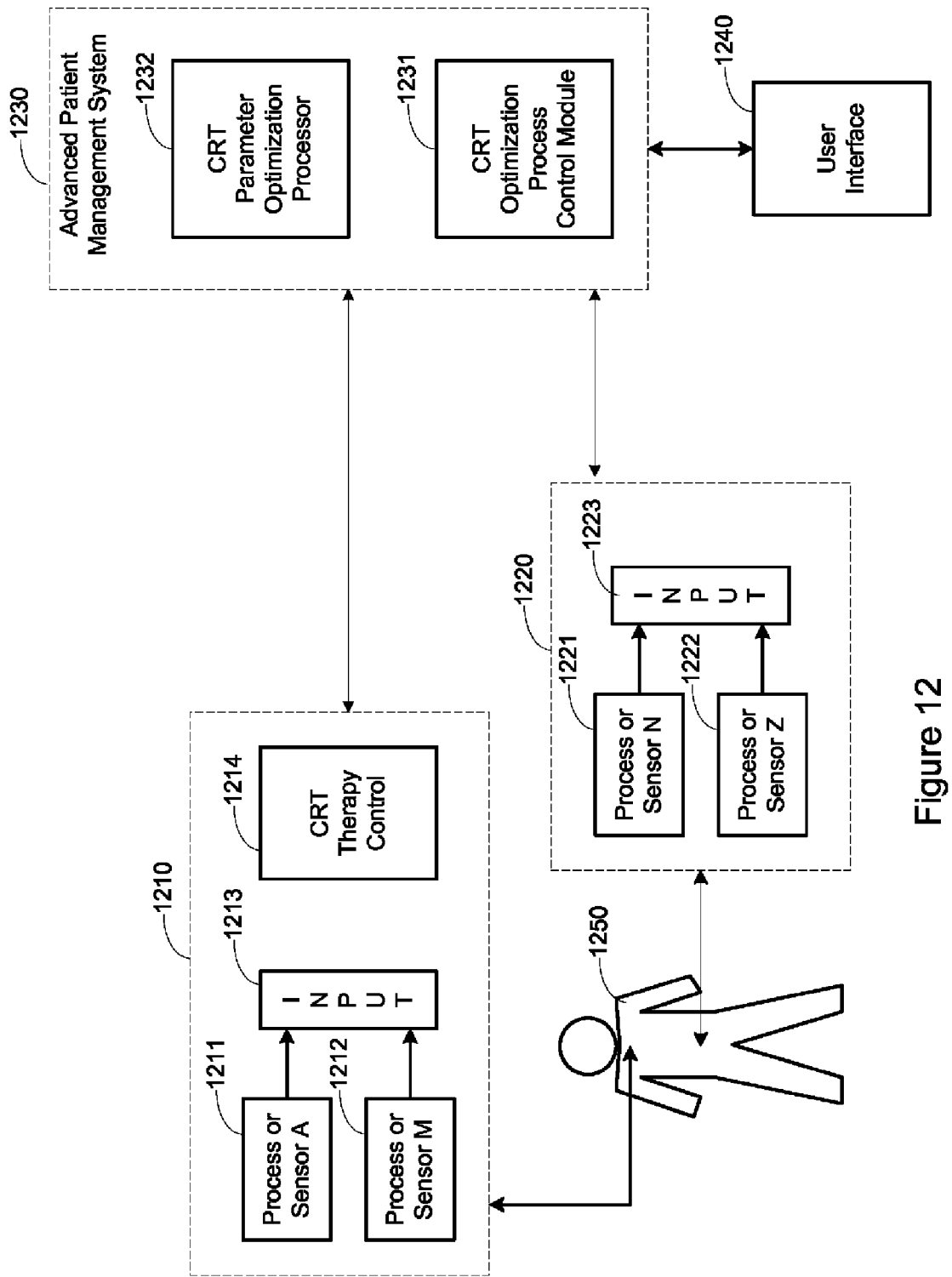
FIG. 12 is a block diagram of a distributed medical system for determining CRT parameters, the distributed medical system including an implantable medical device and an advanced patient management system in accordance with embodiments of the present invention.

FIG. 12 illustrates a CRT parameter optimization system configured as a distributed system. In this embodiment, some components of the CRT parameter optimization system are located in an implantable therapy device 1210, such as a pacemaker, and some components are located in a patient-external advanced patient management (APM) system 1230 coupled to the implantable device 1210 and/or to a patient-external device 1220. In the particular implementation depicted, the pacemaker 1210 is capable of providing CRT therapy.

Other arrangements for the distributed system are also possible, and it is not intended that the CRT optimization system be limited to any particular configuration. For example, in some configurations, the CRT optimization process modules 1211, 1212, 1221, 1222 may be implemented in the APM system. In such a configuration, the APM system may receive sensor information from the implantable and/or patient external devices 1210, 1220, perform the CRT optimization processes to generate recommended parameters and perform CRT parameter optimization as described herein. In other configurations, only an implantable device 1210 may be used to implement the CRT optimization processes. In yet other configurations, only a patient-external device 1220 may be used to implement the CRT optimization processes. In yet other configurations, either the patient external 1220 or implantable 1210 device, or both, may provide the CRT parameter optimization and CRT optimization process control functions. Numerous other configurations for implementing the CRT optimization processes described herein are possible and are considered to be within the scope of the present invention.

The pacemaker 1210 is associated with circuitry for CRT optimization processes or sensors A 1211 through M 1212. In one configuration, the CRT optimization processes provide recommended CRT parameters through input circuitry 1213. The recommended parameters and/or other information is transmitted via a wireless connection to a patient-external advanced patient management (APM) system 1230.

The CRT optimization system may also include a patient-external device 1220. The patient external device is associated with circuitry for CRT optimization processes or sensors N 1221 through Z 1222. The CRT optimization processes/sensors provide recommended CRT parameters through input circuitry 1223. In one example, the patient external device 1220 may include a cardiopulmonary exercise testing system that senses cardiopulmonary variables such as ventilation, heart rate, expired oxygen, expired carbon dioxide, and/or other cardiopulmonary variables. Recommended CRT therapy parameters may be derived from these sensed variables. The recommended CRT parameters and/or other information acquired by the patient-external device may be transmitted via a wireless or wired connection to the APM system 1230.

The APM system 1230 may provide various diagnostic and/or therapeutic functions including CRT parameter optimization functions as described herein. A user interface is coupled to the APM 1230 and allows a physician to remotely monitor cardiac functions, as well as other patient conditions. Alternatively, or additionally, cardiac functions, and other patient conditions may be automatically monitored by the APM system 1230. Methods, structures, and/or techniques described herein, which may be adapted to provide for remote patient/device monitoring, diagnosis, therapy control, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the particular implementation depicted in FIG. 12, the APM system 1230 houses the CRT optimization process control module 1231 and the CRT parameter optimization processor 1232. As previously described, the CRT optimization process control module 1231 may select or rank various CRT optimization processes 1211, 1212 and/or sensors for implementation. Control signals for controlling the CRT optimization processes 1211, 1212 are transmitted wirelessly from the APM system 1230 to the pacemaker 1210.

The CRT parameter optimization processor 1232 determines CRT parameters such as through combining the recommendations of the selected and/or ranked CRT optimization processes 1211, 1212 which may be selectably implemented and/or ranked. Control signals for controlling CRT based on the CRT parameters are provided to the CRT therapy control unit 1214 of the pacemaker 1210 via the wireless link. The pacemaker 1210 delivers CRT to the patient 1250. The APM system 1230 is coupled to a user interface 1240 to allow a physician or other human analyst to view recommended CRT optimization parameters, CRT parameters, to rank or select CRT optimization processes or sensors and/or to enter or view various information related to CRT.

Figure 13:
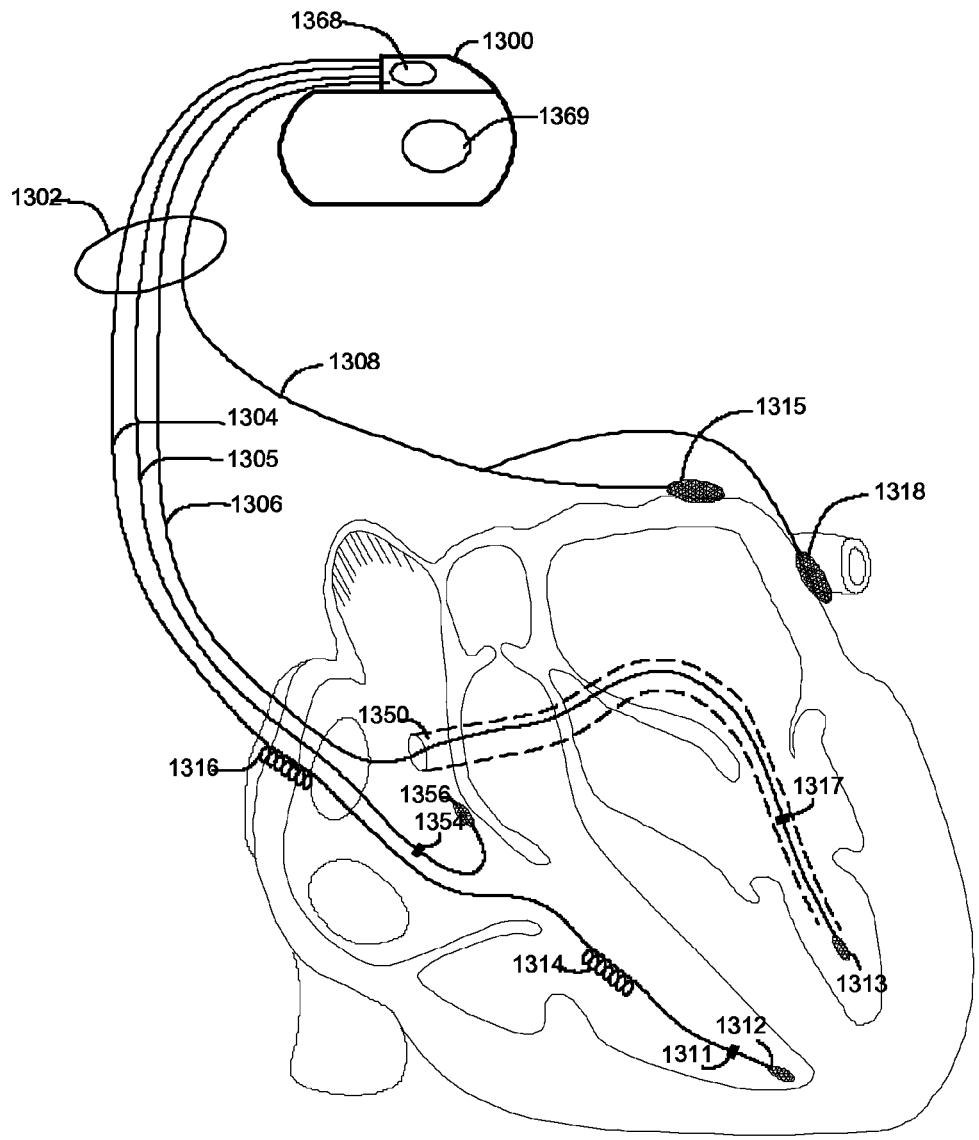
FIG. 13 is a partial view of an implantable cardiac rhythm management system that may be used to implement one, some, or all functions of CRT parameter determination in accordance with embodiments of the present invention.

Referring now to FIG. 13, there is illustrated an embodiment of a patient implantable medical device configured to perform some or all of the CRT parameter optimization functions in accordance with the present invention. The medical device may include various components used for CRT parameter optimization in accordance with embodiments of the present invention, including, for example, mechanical sensors, pressure sensors, impedance sensors, EGM sensors, leadless ECG sensors, HRV sensors, heart sound sensors, and/or other sensors used for CRT parameter optimization. The medical device may include software and/or circuitry configured to implement one or more CRT optimization processes configured to return recommended CRT parameters. The medical device may further include software and/or circuitry configured to implement CRT optimization process control functions and/or CRT parameter optimization functions as previously described. The medical device may include communications circuitry for communicating through a wireless link with a remote patient-external device.

The medical device in FIG. 13 includes a CRM device 1300 electrically and physically coupled to a lead system 1302. The housing and/or header of the CRM device 1300 may incorporate one or more electrodes 1368, 1369 used to provide electrical stimulation energy to the heart and to sense cardiac electrical activity. The CRM device 1300 may utilize all or a portion of the CRM device housing as a can electrode 1369. The CRM device 1300 may include an indifferent electrode 1368 positioned, for example, on the header or the housing of the CRM device 1300. If the CRM device 1300 includes both a can electrode 1369 and an indifferent electrode 1368, the electrodes 1368, 1369 typically are electrically isolated from each other.

The lead system 1302 is used to detect cardiac electrical signals produced by the heart and to provide electrical energy to the heart under certain predetermined conditions to treat cardiac arrhythmias and impaired cardiac synchronization. The lead system 1302 may include one or more electrodes used for pacing, sensing, and/or defibrillation. In the embodiment shown in FIG. 13, the lead system 1302 includes an intracardiac right ventricular (RV) lead system 1304, an intracardiac right atrial (RA) lead system 1305, an intracardiac left ventricular (LV) lead system 1306, and an epicardial left atrial (LA) lead system 1308. The lead system 1302 of FIG. 13 illustrates one embodiment that may be used for delivery of CRT. Other leads and/or electrodes may additionally or alternatively be used.

The lead system 1302 may include intracardiac leads 1304, 1305, 1306 implanted in a human body with portions of the intracardiac leads 1304, 1305, 1306 inserted into a heart. The intracardiac leads 1304, 1305, 1306 include various electrodes positionable within the heart for sensing electrical activity of the heart and for delivering electrical stimulation energy to the heart, for example, pacing pulses and/or defibrillation shocks.

As illustrated in FIG. 13, the lead system 1302 may include one or more epicardial leads 1308 having electrodes, e.g., epicardial electrodes, positioned at locations outside the heart for sensing and pacing one or more heart chambers.

The right ventricular lead system 1304 illustrated in FIG. 13 includes a superior vena cava (SVC)-coil 1316, a right ventricular (RV)-coil 1314, an RV-ring electrode 1311, and an RV-tip electrode 1312. The right ventricular lead system 1304 extends through the right atrium and into the right ventricle. In particular, the RV-tip electrode 1312, RV-ring electrode 1311, and RV-coil electrode 1314 are positioned at appropriate locations within the right ventricle for sensing and delivering electrical stimulation pulses to the heart. The SVC-coil 1316 is positioned at an appropriate location within the right atrium or a major vein leading to the right atrium.

In one configuration, the RV-tip electrode 1312 referenced to the can electrode 1369 may be used to implement unipolar pacing and/or sensing in the right ventricle. Bipolar pacing and/or sensing in the right ventricle may be implemented using the RV-tip 1312 and RV-ring 1311 electrodes. In yet another configuration, the RV-ring 1311 electrode may optionally be omitted, and bipolar pacing and/or sensing may be accomplished using the RV-tip electrode 1312 and the RV-coil 1314, for example. The right ventricular lead system 1304 may be configured as an integrated bipolar pace/shock lead. The RV-coil 1314 and the SVC-coil 1316 are defibrillation electrodes.

The left ventricular lead 1306 includes an LV distal electrode 1313 and an LV proximal electrode 1317 located at appropriate locations in or about the left ventricle for pacing and/or sensing the left ventricle. The left ventricular lead 1306 may be guided into the right atrium of the heart via the superior vena cava. From the right atrium, the left ventricular lead 1306 may be deployed into the coronary sinus ostium, the opening of the coronary sinus 1350. The lead 1306 may be guided through the coronary sinus 1350 to a coronary vein of the left ventricle. This vein is used as an access pathway for leads to reach the surfaces of the left ventricle which are not directly accessible from the right side of the heart. Lead placement for the left ventricular lead 1306 may be achieved via subclavian vein access and a preformed guiding catheter for insertion of the LV electrodes 1313, 1317 adjacent to the left ventricle.

Unipolar pacing and/or sensing in the left ventricle may be implemented, for example, using the LV distal electrode referenced to the can electrode 1369. The LV distal electrode 1313 and the LV proximal electrode 1317 may be used together as bipolar sense and/or pace electrodes for the left ventricle. The left ventricular lead 1306 and the right ventricular lead 1304, in conjunction with the CRM device 1300, may be used to provide cardiac resynchronization therapy such that the ventricles of the heart are paced substantially simultaneously, or in phased sequence, to provide enhanced cardiac pumping efficiency for patients suffering from heart failure.

The right atrial lead 1305 includes a RA-tip electrode 1356 and an RA-ring electrode 1354 positioned at appropriate locations in the right atrium for sensing and pacing the right atrium. In one configuration, the RA-tip 1356 referenced to the can electrode 1369, for example, may be used to provide unipolar pacing and/or sensing in the right atrium. In another configuration, the RA-tip electrode 1356 and the RA-ring electrode 1354 may be used to effect bipolar pacing and/or sensing.

FIG. 13 illustrates one embodiment of a left atrial lead system 1308. In this example, the left atrial lead 1308 is implemented as an epicardial lead with LA distal 1318 and LA proximal 1315 electrodes positioned at appropriate locations outside the heart for sensing and pacing the left atrium. Unipolar pacing and/or sensing of the left atrium may be accomplished, for example, using the LA distal electrode 1318 to the can 1369 pacing vector. The LA proximal 1315 and LA distal 1318 electrodes may be used together to implement bipolar pacing and/or sensing of the left atrium. The left atrial lead 1308 and the right atrial lead 1305, in conjunction with the CRM device 1300, may be used to provide cardiac resynchronization therapy such that the atria of the heart are paced substantially simultaneously, or in phased sequence, toprovide enhanced cardiac pumping efficiency for patients suffering from heart failure.

The components, functionality, and structural configurations depicted herein are intended to provide an understanding of various features and combination of features that may be incorporated in an implantable or patient-external medical device or system. It is understood that a wide variety of such device or system configurations are contemplated, ranging from relatively sophisticated to relatively simple designs. As such, particular implantable/external or cardiac monitoring and/or stimulation device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for operating a cardiac device to algorithmically determine a value of a parameter for use in delivery of cardiac resynchronization therapy (CRT), the method comprising:
   implementing a first cardiac resynchronization therapy (CRT) optimization process by analyzing a first set of physiological signals and returning a first recommended value for a CRT parameter based on the first set of physiological signals;
   adjusting a CRT parameter value search range of at least one additional CRT optimization process based on the first recommended value, the first CRT optimization process based on a different process of optimization with respect to the at least one additional CRT optimization process;
   implementing the at least one additional CRT optimization process by analyzing a second set of physiological signals and using the adjusted value search range to return an additional recommended value for the CRT parameter for each additional CRT optimization process; and
   determining the value of the CRT parameter for use in delivery of CRT by the cardiac device based on the additional recommended values returned by the one or more additional CRT optimization processes.

2. The method of claim 1, wherein implementing the at least one additional CRT optimization process comprises sequentially implementing a plurality of additional CRT optimization processes that are different from the first CRT optimization process.

3. The method of claim 2, wherein sequentially implementing the plurality of additional CRT optimization processes comprises sequentially implementing the plurality of additional CRT optimization processes according to a predetermined order indicated by a physician.

4. The method of claim 1, wherein determining the value of the CRT parameter comprises combining recommended values returned by two or more different CRT optimization processes of the first CRT optimization process and the at least one additional CRT optimization process.

5. The method of claim 1, wherein implementing the at least one additional CRT optimization process comprises:
   implementing a plurality of additional CRT optimization processes, including implementing a first group of the plurality of CRT optimization processes and implementing a second group of the plurality of additional CRT optimization processes if the recommended values returned by the first group produce an ambiguity in selection of the value of the CRT parameter, wherein each CRT optimization process of the first group is different from each CRT optimization process of the second group.

6. The method of claim 1, wherein implementing the at least one additional CRT optimization process comprises selectively implementing the at least one additional CRT optimization process based on patient condition information acquired from at least one of an implantable or patient-external device.

7. The method of claim 1, wherein the first CRT optimization process is different from the at least one additional CRT optimization process in that the processes are based on different types of physiological signals.

8. The method of claim 1, wherein the first CRT optimization process is different from each of the at least one additional CRT optimization process in that one process is morphology based and the other process is timing based.

9. The method of claim 1, wherein the CRT parameter comprises at least one of a pacing energy, a pacing waveform, a pacing site, a pacing mode, a pacing rate, an atrioventricular delay, an interventricular delay, and an interatrial delay.

10. The method of claim 1, further comprising implementing CRT using the determined value of the CRT parameter.

11. A medical system, comprising:
sensor circuitry configured to sense physiological signals;
a first cardiac resynchronization therapy (CRT) optimization module configured to implement a first CRT value optimization process, the first CRT optimization module configured to analyze one or more of the sensed physiological signals and to return a first recommended value for a CRT delivery parameter as part of implementation of the first CRT value optimization process;
one or more additional CRT optimization modules configured to implement one or more additional CRT value optimization processes, each additional CRT optimization module configured to analyze one or more of the sensed physiological signals and to use a CRT parameter value search range adjusted using the first recommended value to return an additional recommended value for the CRT delivery parameter as part of implementation of a respective one of the one or more additional CRT value optimization processes, the first CRT value optimization process based on a different process of optimization with respect to the one or more additional CRT optimization processes; and
a processor configured to determine a value of the CRT delivery parameter for use in implementing CRT based on the additional recommended values returned by the one or more additional CRT optimization modules.

12. The medical system of claim 11, wherein the first CRT optimization module is configured to analyze a first one or more physiological signals as part of implementation of the first CRT value optimization process and the one or more additional CRT optimization modules is configured to analyze a second one or more physiological signals as part of implementation of a respective one of the one or more additional CRT value optimization processes, wherein the first one or more physiological signals and the second one or more physiological signals are different signal types.

13. The medical system of claim 11, further comprising a control module, wherein the one or more additional CRT optimization modules are configured to implement multiple of the one or more additional CRT value optimization processes sequentially and the control module is configured to automatically determine an order of implementation of the multiple of the one or more additional CRT optimization processes.

14. The medical system of claim 11, wherein the first CRT value optimization process is different from the one or more additional CRT value optimization processes in that the one or more additional CRT value optimization processes are based on different types of physiological signals with respect to the first CRT value optimization process.

15. The medical system of claim 11, further comprising a user interface, wherein an order of implementation of the one or more additional CRT optimization processes is determined at least in part based on input acquired from a patient-external device.

16. The medical system of claim 11, wherein the processor is configured to combine the first recommended value and at least one additional recommended value returned by the one or more additional CRT optimization modules and to determine the value of the CRT parameter based on the combined recommended values.

17. The medical system of claim 11, wherein at least one component of the medical system is disposed within a housing of an implantable cardiac rhythm management system.

18. The medical system of claim 11, wherein the first CRT value optimization process is different from the one or more additional CRT value optimization processes in that one process is morphology based and the other process is timing based.

19. The medical system of claim 11, wherein the processor is configured to automatically select one recommended value from multiple recommended values returned by multiple of the one or more additional CRT optimization modules as the value of the CRT parameter.

20. The medical system of claim 11, wherein at least one of the CRT optimization modules is selected for implementation based on patient conditions.

21. The medical system of claim 11, wherein the CRT parameter comprises one or more pacing parameters.

22. The medical system of claim 11, further comprising a CRT delivery module configured to deliver the CRT using the determined value of the CRT parameter.

23. A system for determining a value of at least one cardiac resynchronization therapy (CRT) parameter, the system comprising:
means for implementing a first cardiac resynchronization therapy (CRT) optimization process by analyzing one or more physiological signals and returning a first recommended value for at least one CRT parameter;
means for implementing one or more additional CRT optimization processes by analyzing one or more physiological signals to return an additional recommended value for the at least one CRT parameter using a value search range that is adjusted based on the first recommended value for each implementation of the one or more additional CRT optimization processes, the first CRT optimization process based on a different process of optimization with respect to each of the one or more additional CRT optimization processes; and
means for determining the value of the at least one CRT parameter for use in delivery of CRT based on the additional recommended values returned by the one or more additional CRT optimization processes.

24. The system of claim 23, further comprising:
means for acquiring information related to CRT optimization; and means for selectively implementing at least one of the first and the one or more additional CRT optimization processes based at least in part on the acquired information.

25. The system of claim 23, wherein the means for determining further comprises means for combining the recommended values returned by the one or more additional CRT optimization processes.

26. The system of claim 23, further comprising means for sequentially implementing the one or more additional CRT optimization processes.

* * * * *